US012698538B2

(12) United States Patent
Harris et al.

(10) Patent No.: US 12,698,538 B2
(45) Date of Patent: Aug. 4, 2026

(54) METHODS FOR PREDICTING EQUINE WEIGHT LOSS PROPENSITY

(71) Applicant: MARS, INCORPORATED, McLean, VA (US)

(72) Inventors: Patricia Ann Harris, Leicestershire (GB); Philippa Kate Taverner, Edinburgh (GB); Caroline McGregor Argo, Edinburgh (GB); Charles James Newbold, Edinburgh (GB); David Hugh Grove-White, Gwynedd (GB)

(73) Assignee: MARS, INCORPORATED, McLean, VA (US)

( * ) Notice: Subject to any disclaimer, the term of this patent is extended or adjusted under 35 U.S.C. 154(b) by 1188 days.

(21) Appl. No.: 17/615,346

(22) PCT Filed: May 29, 2020

(86) PCT No.: PCT/GB2020/051310
§ 371 (c)(1),
(2) Date: Nov. 30, 2021

(87) PCT Pub. No.: WO2020/240203
PCT Pub. Date: Dec. 3, 2020

(65) Prior Publication Data
US 2022/0220540 A1     Jul. 14, 2022

(30) Foreign Application Priority Data

May 31, 2019    (GB) ..................................... 1907782

(51) Int. Cl.
| | |
|---|---|
| *C12Q 1/689* | (2018.01) |
| *C12N 15/10* | (2006.01) |
| *G16B 10/00* | (2019.01) |
| *G16B 30/10* | (2019.01) |
| *G16B 40/00* | (2019.01) |

(52) U.S. Cl.
CPC ......... *C12Q 1/689* (2013.01); *C12N 15/1065* (2013.01); *G16B 10/00* (2019.02); *G16B*

*30/10* (2019.02); *G16B 40/00* (2019.02); *C12Q 2600/124* (2013.01); *G01N 2800/02* (2013.01)

(58) Field of Classification Search
None
See application file for complete search history.

(56) References Cited

FOREIGN PATENT DOCUMENTS

WO      WO 2013/136069 A2      9/2013

OTHER PUBLICATIONS

Morrison PK. The equine gastrointestinal microbiome: impacts of age and obesity. Frontiers in Microbiology 9: 1-13. (Year: 2018).*
Elzinga SE. Comparison of the fecal microbiota in horses with equine metabolic syndrome and metabolically normal controls fed a similar all-forage diet. Journal of Equine Veterinary Science 44: 9-16. (Year: 2016).*
Cox, L.M. et al., "Antibiotics shape microbiota and weight gain across the animal kingdom," Animal Frontiers, vol. 6, No. 3, pp. 8-14, Jul. 2016.
International Search Report mailed Nov. 9, 2020 in International Application No. PCT/GB2020/051310.
Morrison, P.K. et al., "The equine gastrointestinal microbiome: impacts of weight-loss," BMC Veterinary Research, vol. 16, No. 1, 78, pp. 1-18, Mar. 2020.
Shepherd, M.L. et al., "Fibre digestibility, abundance of faecal bacteria and plasma acetate concentrations in overweight adult mares," Journal of Nutritional Science, vol. 3, E10, pp. 1-11, 2014.

* cited by examiner

*Primary Examiner* — Olivia M. Wise
*Assistant Examiner* — Robert J. Kallal
(74) *Attorney, Agent, or Firm* — Baker Botts L.L.P.

(57)      ABSTRACT

The invention provides methods of predicting the weight loss propensity of an animal of the genus *Equus*, through the assessment of various markers in a sample obtained from the animal. Such markers include fermentation products and/or metabolites thereof such as volatile fatty acids, indicators of bacterial population diversity, and the abundance/relative abundance of specific bacterial *taxa*.

14 Claims, 15 Drawing Sheets
Specification includes a Sequence Listing.

Tenericutes  Proteobacteria  Spirochaetes  Unclassified

Fibrobacteres  Firmicutes  Bacteroidetes

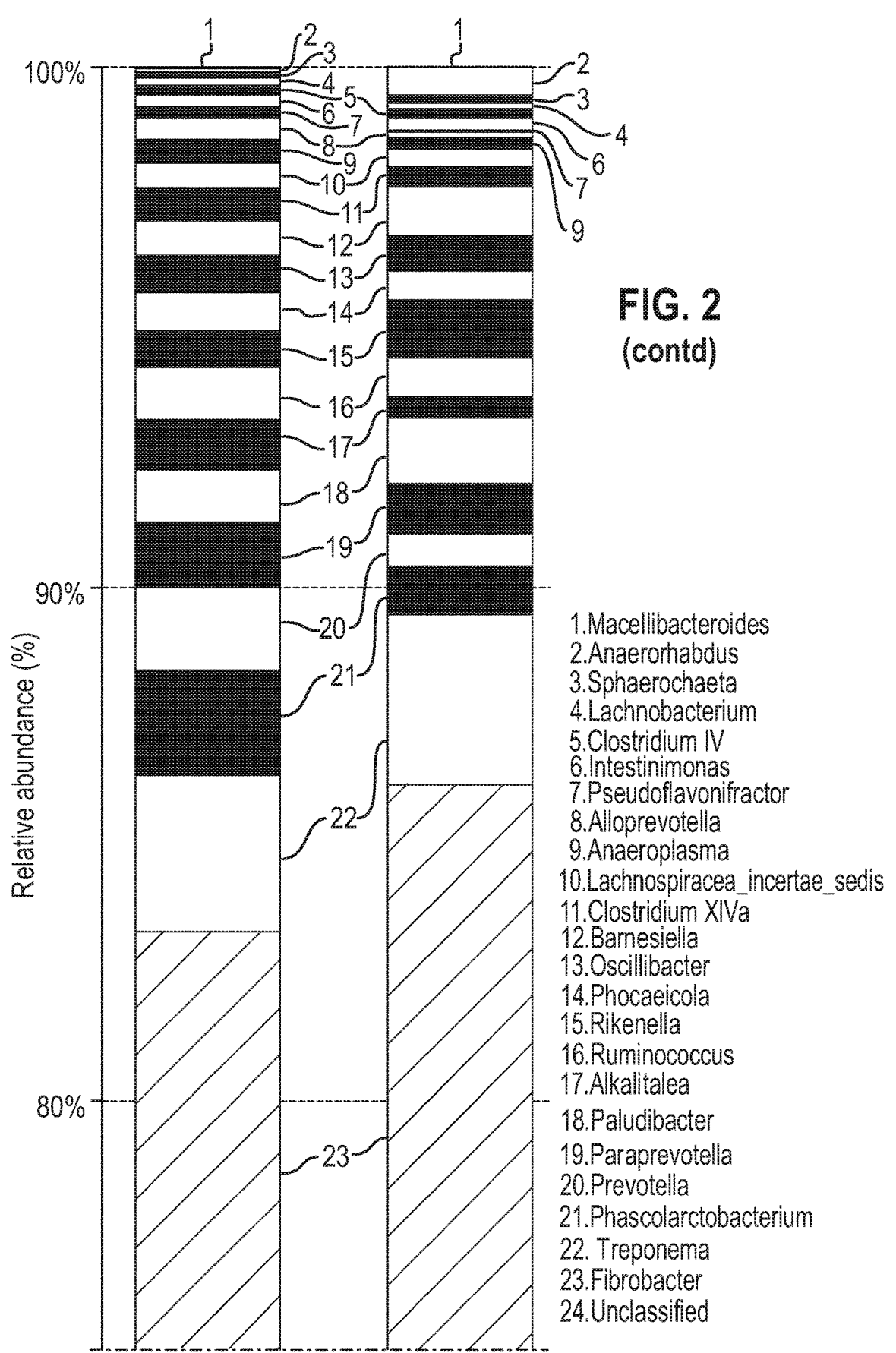

FIG. 2
(contd)

1. Macellibacteroides
2. Anaerorhabdus
3. Sphaerochaeta
4. Lachnobacterium
5. Clostridium IV
6. Intestinimonas
7. Pseudoflavonifractor
8. Alloprevotella
9. Anaeroplasma
10. Lachnospiracea_incertae_sedis
11. Clostridium XIVa
12. Barnesiella
13. Oscillibacter
14. Phocaeicola
15. Rikenella
16. Ruminococcus
17. Alkalitalea
18. Paludibacter
19. Paraprevotella
20. Prevotella
21. Phascolarctobacterium
22. Treponema
23. Fibrobacter
24. Unclassified Standardise Samples by Total
Transform: Square root
Resemblance: S17 Bray-Curtis similarity

*Group average*

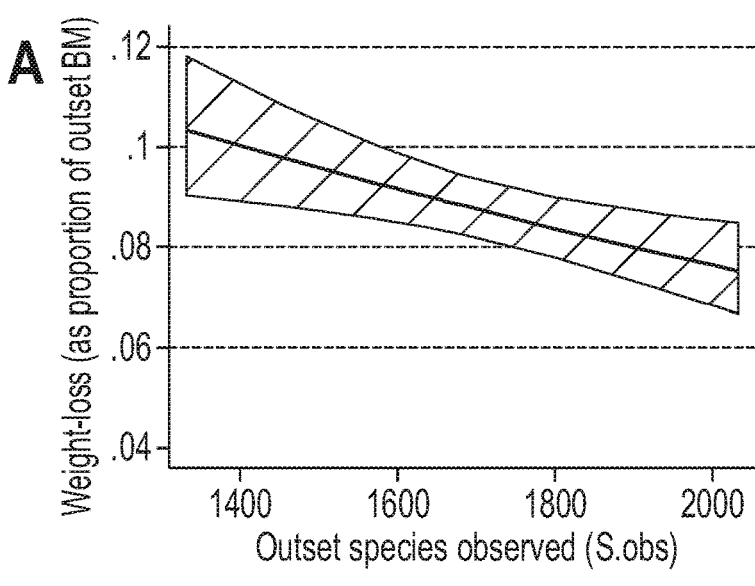
FIG. 8
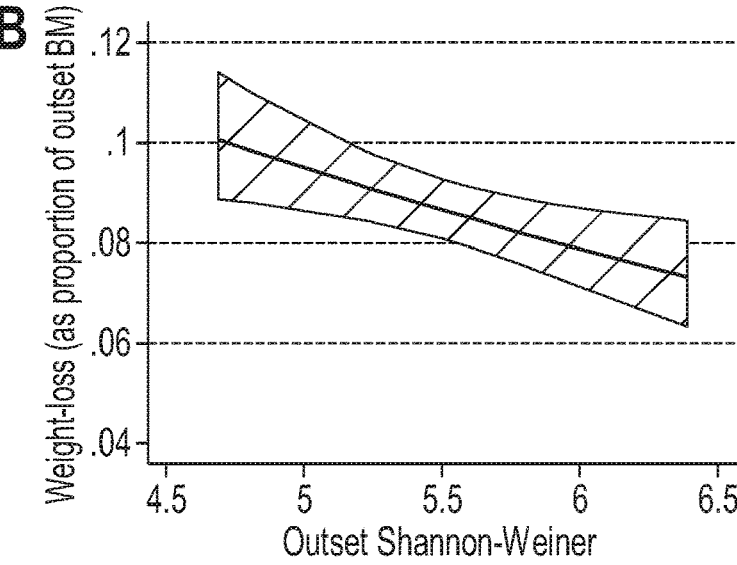
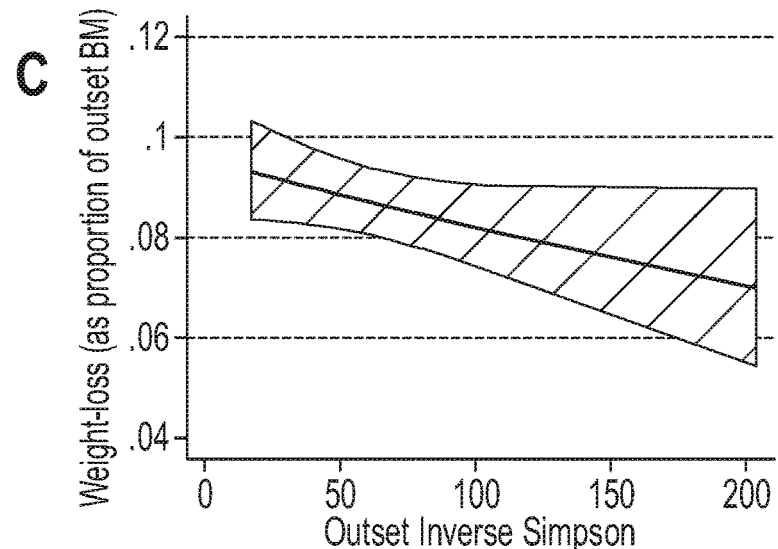

A

B

C

D

METHODS FOR PREDICTING EQUINE WEIGHT LOSS PROPENSITY

CROSS REFERENCE TO RELATED APPLICATIONS

This application is a U.S. National Stage Patent Application under 35 U.S.C. § 371 of International Application No. PCT/GB2020/051310, filed on May 29, 2020, which claims the benefit of priority to GB Application No. 1907782.5, filed on May 31, 2019, the contents of each of which are incorporated herein by reference in their entireties, and to each of which priority is claimed.

SEQUENCE LISTING

The specification further incorporates by reference the Sequence Listing submitted herewith via EFS on Nov. 30, 2021. Pursuant to 37 C.F.R. § 1.52(e)(5), the Sequence Listing text file, identified as 0692690503SL.txt, is 662 bytes and was created on Nov. 18, 2021. The Sequence Listing, electronically filed herewith, does not extend beyond the scope of the specification and thus does not contain new matter.

TECHNICAL FIELD

The invention is in the field of methods for predicting the potential weight loss of an Equine.

BACKGROUND TO THE INVENTION

Bacteria residing in the gastrointestinal tract of all species play a fundamental role in host health and whole-body metabolism, whereby disruptions to energy balance, such as observed in obesity and associated metabolic diseases, are associated with dysbiosis of the gut microbiota[1-4]. Associations between obesity and the composition of the gut microbiome have been identified in humans[5,6], dogs[7], and more recently in ponies[8].

Horses and ponies are adapted to consume high-fibre diets, whereby the microbial fermentation of dietary fibre in the hindgut produces volatile fatty acids (VFA) including acetate, propionate and butyrate that together contribute a significant proportion of the individual animal's daily energy requirements[9]. A combination of increased nutrient-dense energy provisions and a lack of exercise has culminated in a high prevalence of obesity in leisure populations of horses and ponies in industrialised nations, and is a key welfare issue[10-12]. Specific breeds and types of horse and ponies (including native and Welsh breeds) have been identified to be more at risk of developing obesity than others, indicating a significant genetic component of obesity development in this species. As for humans, not all horses and ponies will lose weight at the same rate when placed on an energy restricted diet (e.g. 1.25% body mass (BM) as dry matter (DM) daily), and some will require further restriction (e.g. to 1.0% BM as DM daily) to elicit expected reductions in BM[13].

To date, studies evaluating the gut microbiome in the horse have generally focused on the impact of diet[14-16] Additionally, associations between the faecal microbiome and chronic laminitis[17] and equine metabolic syndrome (EMS)[18] have been evaluated. Although no studies have yet been conducted to describe changes in the composition of the faecal microbiome following weight-loss in ponies, two studies have evaluated the stability of the faecal microbiome in groups of horses and ponies across time. Across a 6-week period at the end of a weight-loss trial, it was identified that 65% of the faecal bacterial community in a group of horses was retained between time points[19], and more recently, the stability of the equine faecal microbiome over a 52-week period was evaluated in a small population of horses maintained at pasture. Therefore, we have some evidence that the equine gut microbiome is influenced by diet and by different disease states. In addition, the effects of age and obesity on the equine faecal microbiome have recently been assessed over a two year period, finding changes predominantly associated with obese state[8].

Accordingly, there is evidence that the equine gut microbiome is influenced by diet and by different disease/metabolic states[8]. However, there remains a need in the art for methods which can predict the weight-loss propensity of equines, allowing for appropriate caloric restriction to be effected by the owner.

SUMMARY OF THE INVENTION

The inventors have developed methods which can predict the weight loss propensity of an animal of the genus *Equus*. This is achieved through the assessment of various markers in a sample obtained from the animal (such as a faecal, blood or urine sample). These include, for example, fermentation products and/or metabolites thereof, such as volatile fatty acids (VFAs), as well as indicators of bacterial population diversity, and/or the abundance (and/or relative abundance) of specific bacterial *taxa*. The methods of the invention can predict likely weight loss as shown in the examples, and in certain embodiments, methods of the invention can be used to make a quantitative prediction of the loss of outset body mass after a period of caloric restriction.

Accordingly, in one aspect, the invention provides a method of predicting the weight loss of an animal of the genus *Equus*, comprising measuring the concentration of one or more fermentation products and/or metabolites thereof (e.g. one or more VFAs) in a sample obtained from the animal; wherein the concentration of the one or more fermentation products and/or metabolites thereof (e.g. the one or more VFAs) is positively associated with the predicted weight loss of the animal. For example, the inventors found concentrations of acetate, butyrate, propionate and branched-chain VFAs prior to a period of caloric restriction to be higher in animals with greater subsequent weight loss (see Example 1; FIG. 9). For example, the concentration of at least 12 mM acetate was found to be an accurate predictor of good weight loss propensity. For example, the inventors have found that such animals were able to lose at least 8% outset body mass after a period of 7 weeks caloric restriction (see FIG. 10). Accordingly, these markers provide a means of predicting weight loss propensity in equines.

In a further aspect, the invention provides a method of predicting the weight loss of an animal of the genus *Equus*, comprising detecting and/or quantifying a plurality of bacterial *taxa* in a sample obtained from the animal, and calculating a diversity measure of the bacterial population present in the sample; wherein the diversity measure is negatively associated with the predicted weight loss of the animal. The inventors found particular diversity measures of the bacterial population (Inverse-Simpson, Shannon-Weiner and number of observed species) prior to a period of caloric restriction to be higher in animals with less subsequent weight loss (see Example 1; FIG. 8). Accordingly, these markers provide a further means of predicting weight loss propensity in equines.

In a further aspect, the invention provides a method of predicting the weight loss of an animal of the genus *Equus* comprising quantifying the abundance and/or relative abundance of (i) bacteria of the genus Sphaerochaeta, and/or (ii) bacteria of the genus *Treponema*, and/or (iii) bacteria of the genus *Anaerovorax* and/or (iv) bacteria of the genus *Mobilitalea*, and/or (v) bacteria of the phylum Actinobacteria, and/or (vi) bacteria of the phylum Spirochaetes, and/or (vii) fibre-fermenting bacteria (such as bacteria of the genus *Fibrobacter*) present in a sample obtained from the animal; wherein the abundance and/or relative abundance of said bacteria is negatively associated with the predicted weight loss of the animal. The inventors found the abundance/relative abundance of such bacteria prior to a period of caloric restriction to be higher in animals with less subsequent weight loss (see Examples 1 and 2; FIGS. 12-14). Accordingly, these further markers provide a further means of predicting weight loss propensity in equines.

The markers used in the above aspects of the invention may be used either alone or combination as a predictor of weight loss. Combinations of these different markers may improve the predictive power of methods of the invention.

BRIEF DESCRIPTION OF DRAWINGS

FIG. 8. Marginal mean plots illustrating predicted changes in proportional weight-loss with outset diversity indices: (A) Species observed, (B) Shannon-Weiner, (C) Inverse Simpson. Shaded area corresponds to 95% CI. n=15.

DISCLOSURE OF THE INVENTION

The Equine

Figure 1:
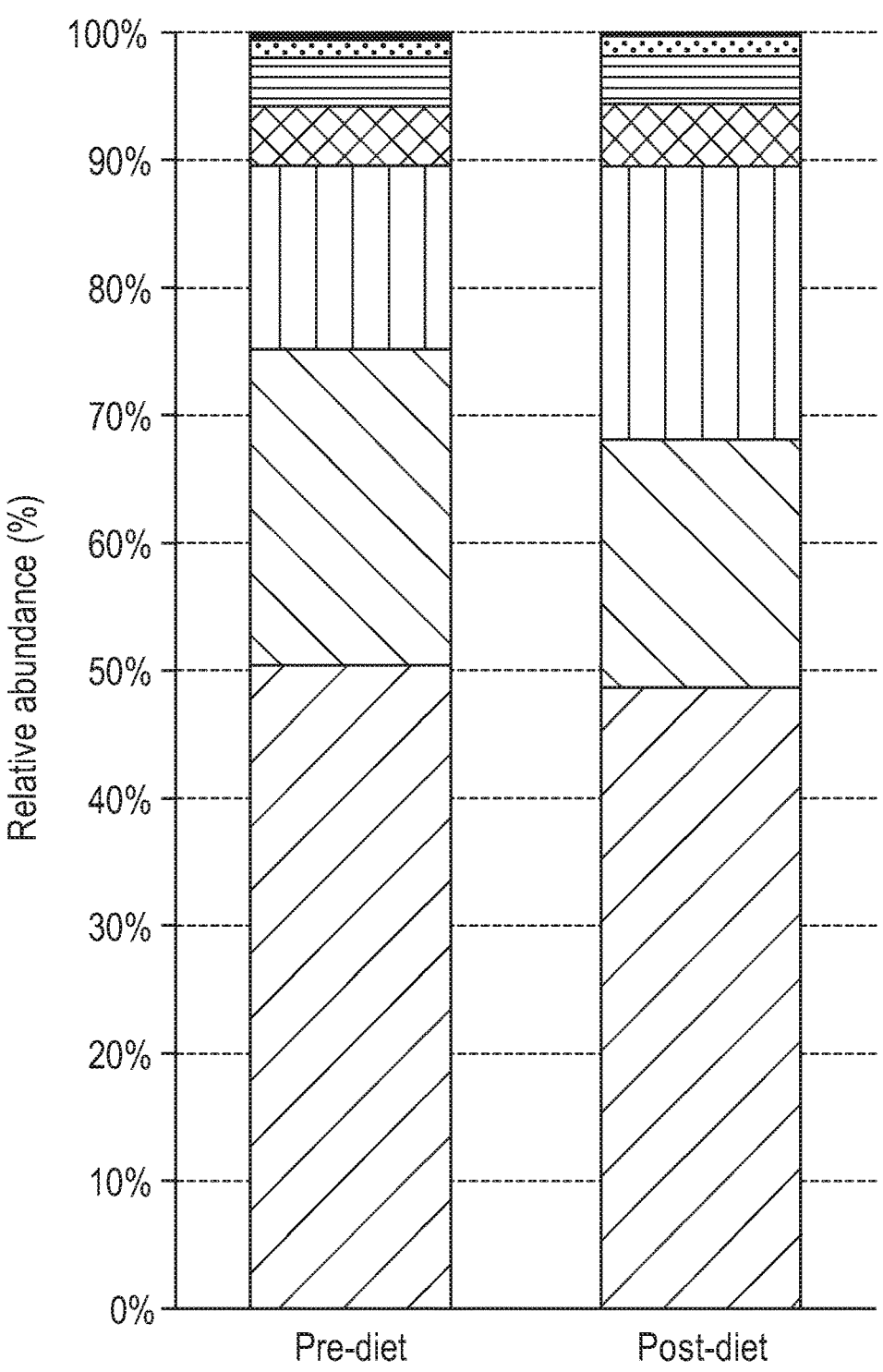
FIG. 1. Stacked histogram illustrating the relative abundance of the dominant bacterial phyla (present at >0.05%) before (pre-diet), and after 7 weeks of dietary restriction (post-diet; n=15).

The methods of the invention can be used to predict the weight loss of an animal of the genus *Equus*.

This genus is part of the Equidae family, which includes numerous extant and extinct species. Species of the genus *Equus* include horses (*Equus caballus*), mules (*Equus mules*), hinnies, wild horses (*Equus ferus*), mountain zebras (*Equus zebra*), African wild asses (*Equus africanus*), domestic donkey (*Equus africanus acinus*), Grevy's zebras (*Equus grevyi*), Asiatic wild asses (*Equus hemionus*), kiangs (*Equus kiang*), and plains zebras (*Equus quagga*). Preferably, the animal is of the species *Equus caballus*, which includes horses and ponies, and more preferably the animal is a pony. The animal of the species *Equus caballus* may be of any age, gender or castration status, and so the invention can be used to assess (without limitation) foals, weanlings, yearlings, colts, fillies, mares, stallions, geldings or rigs. Any and all breeds of animals of the genus *Equus*, preferably of the species *Equus caballus*, can be assessed using methods of the invention.

The methods of the invention are preferably performed on a sample from an animal of the genus *Equus* which is at least overweight prior to commencing the period of caloric restriction. The weight status of the equine is preferably assessed by Body Condition Scoring (BCS)[20] which is a widely used method for estimating body fatness in horses and ponies which combines visual appraisal and palpation of subcutaneous body fat across several body regions (e.g. neck, withers, loin, tailhead, ribs, shoulder), typically scoring each region from 1-9 separately before an overall average is calculated. As used herein, "overweight" is preferably defined as the animal having a BCS score of greater than 6/9 (6 out of 9), with "obese" preferably defined as greater than 7/9 (7 out of 9). Although BCS scoring is the preferred method of assessing weight status/body fatness, other techniques available to the skilled person, such as deuterium oxide dilution and bioelectrical impedance analysis, can also be used.

Weight Loss

As is well-known in the art, "weight loss" refers to a reduction in body mass. In the context of the invention, the weight loss refers to a reduction in the body mass of an animal of the genus *Equus* (for example in response to a change in diet such as caloric restriction, and/or increased exercise). Preferably, methods of the invention are used to predict weight loss in response to caloric restriction (with or without increased exercise).

The rate of weight loss will depend on a number of factors including, but not limited to, the initial body fat content of the animal, the degree of caloric restriction, time over which the caloric restriction is applied and the season. As a guide, a good rate of weight loss would be ≥0.4% of body mass/week from the second week after being put on a dietary restriction of 1.25% body mass of dry matter (DM) of low calorie feed. At a dietary restriction of 1% DM of a low calorie feed, a good rate of weight loss could be ≥0.7% of body mass/week from the second week after being put on the dietary restriction.

In colder temperatures or during periods of adverse weather (rain/wind), a bigger weight loss can be expected as the animal uses up more calories to maintain its body temperature. Thus, during periods of colder temperatures (e.g. in the winter), at a dietary restriction of 1% DM of a low calorie feed, a good rate of weight loss would be ≥0.9% of body mass/week from the second week after being put on the dietary restriction.

Preferably, this weight loss is detected between the second and tenth week after initiation of the low calorie diet. This is to take into account an initial high weight loss due to potential loss of gut fill. Furthermore, the inventors have found that rate of weight loss tends to decrease around 10-12 weeks of feed restriction, at which time point, if further weight loss is needed it may be necessary to either increase the exercise load if possible and/or decrease the calorie intake further if possible taking into physiological and behavioural requirements of the animal.

Caloric restriction refers generally to a reduction in the calorie intake of the animal, as compared to when the animal is free to eat ad libitum. As used herein, caloric restriction for weight management purposes may be defined as the animal of the genus *Equus* ingesting a mean of less than 1.50%, 1.25%, 1.20%, 1.15%, 1.10%, 1.05% or 1.00% of its body mass in dry matter per day. Preferably, caloric restriction is defined as the animal of the genus *Equus* ingesting a mean of less than 1.50%, 1.25% or 1.10%, more preferably less than 1.25% or 1.10%, such as about 1%, of its body mass in dry matter per day. Preferably, as referred to herein, "dry matter" comprises (and more preferably consists essentially of, or consists of) fibrous material, such as preserved grass such as hay or hay substitutes (preferably, plus for nutritional purposes a low calorie vitamin/mineral and protein balancer). In the examples, caloric restriction was effected by a diet of approximately 1.0% body mass in dry matter as hay, per day plus balancer (see Materials and Methods). Water should be provided ad libitum during periods of caloric restriction, as per the examples. A basal level of exercise is also recommended during the period of caloric restriction, potentially both structured (e.g. ridden, walking in hand or lunging etc.) and unstructured (e.g. turn out into large barns/dry lots/indoor or outdoor schools or onto pasture with appropriate muzzles to prevent or limit feed intake) including pasture daily, preferably at least 30 minutes free exercise as per the examples (see Materials and Methods). Certain animals may not be able to undertake structured or unstructured exercise for all or part of the time they are under a calorie restriction protocol for veterinary or behavioural reasons.

The period of caloric restriction to ensure adequate weight loss may need to be maintained for at least 4, 6, 8, 10, 12, 14 or 16 weeks. Preferably, the period of caloric restriction is to be maintained for at least 6 or 7, and more preferably at least 7 weeks (as per the examples). Periods of caloric restriction may also be effected in cycles, for example by restricting caloric intake for a defined number of weeks, monitoring the resultant weight loss and then restricting again if appropriate. Periods of time may refer to continuous or aggregate periods, but preferably refer to continuous periods.

Once provided with a prediction concerning the weight loss of the animal of the genus *Equus* by methods of the invention, the owner may then adjust the diet and/or exercise level (in particular, the diet) of the animal of the genus *Equus*, depending on the desired weight loss over a given time period. For example, an animal with reduced predicted weight loss may be placed on a diet of greater caloric restriction (e.g. around 1% body mass in dry matter per day), or for a longer duration, than originally intended, to ensure that the desired weight loss is achieved. Conversely, an animal with excessive predicted weight loss may be placed on a diet of lesser caloric restriction, or for a shorter duration, than originally intended (e.g. around 1.5% body mass in dry matter per day, or around 1% but for a relatively short duration such as <10 weeks). This has the benefit of avoiding unnecessary health and behavioural risks such as hyperlipaemia (special care is required with donkeys and pregnant mares with any calorie restriction), and foraging replacement behaviours such as crib-biting/windsucking. Accordingly, the invention is useful in ensuring that an animal of the genus *Equus* is placed on a diet that is as appropriate as possible for achieving a desired level of weight loss, given the variance in weight loss propensity that exists between individuals[13].

Fermentation Products and/or Metabolites Thereof as a Predictor of Weight Loss

Figure 9:
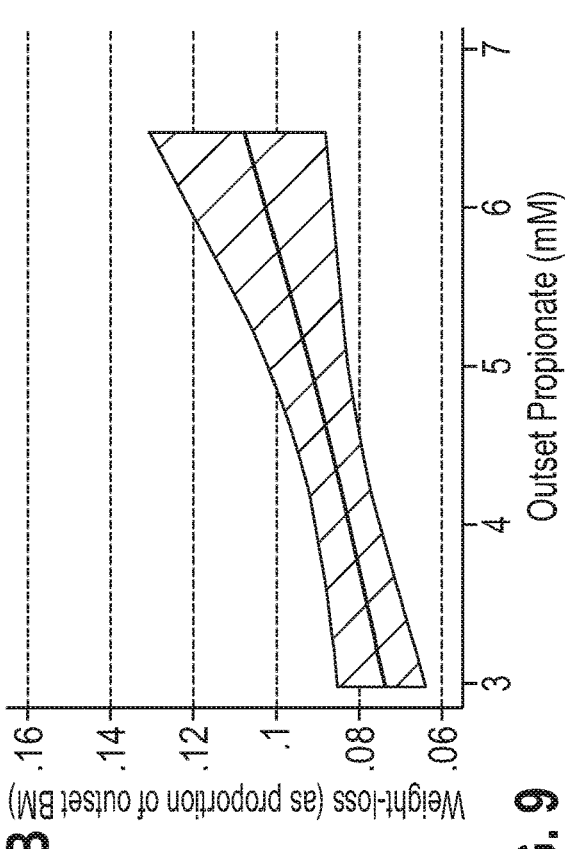
FIG. 9. Marginal mean plots illustrating predicted changes in proportional weight-loss with outset VFA concentrations: (A) Acetate, (B) Propionate, (C) Butyrate, (D) Branched chained volatile fatty acids (BCVFA). Shaded area corresponds to 95% CI. n=15.
Figure 9:
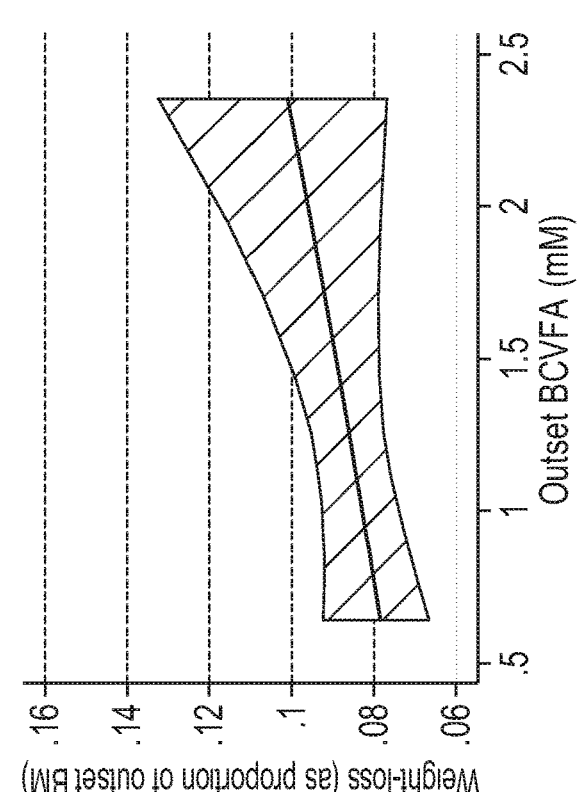
Figure 9:
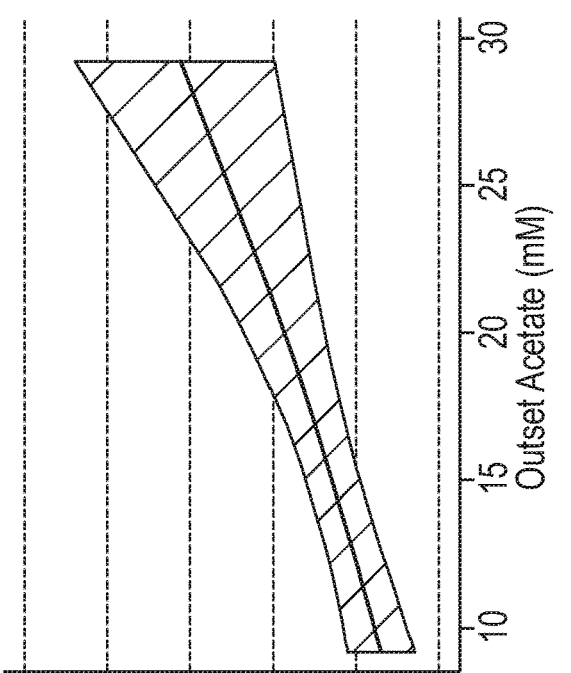
Figure 9:
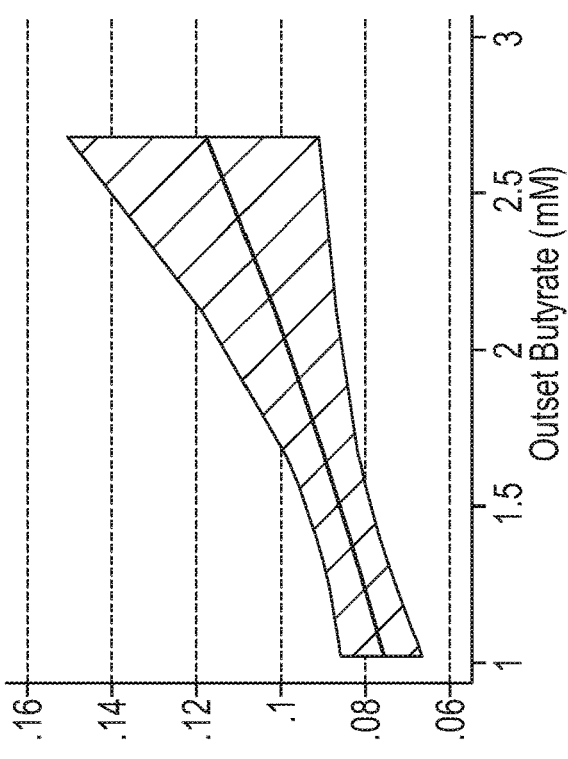

According to one aspect of the invention, the concentration of one or more fermentation products and/or metabolites thereof in a sample obtained from an animal of the genus *Equus* is used as a predictor of weight loss, preferably weight loss in response to caloric restriction. As shown in the examples, outset concentrations of various fermentation products (in particular VFAs) and/or metabolites thereof are positively associated with subsequent weight loss. "Positively associated" means there exists a positive correlation between said concentrations and subsequent weight loss (see FIG. 9 as an example) or, expressed differently, a higher concentration of the fermentation product and/or metabolite thereof in the sample is predictive of more subsequent weight loss than a lower concentration, and vice versa. Animals which show a higher concentration of one or more fermentation products and/or metabolites thereof in the sample can generally be expected to lose weight faster compared to animals which have a lower concentration of the one or more fermentation products and/or metabolites thereof, on an equivalent diet. In addition or alternatively, animals with a higher concentration of one or more fermentation products and/or metabolites thereof can be expected to lose more weight in the same time span compared to animals with a lower concentration of the one or more fermentation products and/or metabolites thereof, on an equivalent diet.

"Fermentation products" refer to the breakdown products of all ingested feedstuffs that are fermented by commensal bacteria in the gastrointestinal tract of the animal. Such feedstuffs include carbohydrates, for example, cellulose, hemicellulose and pectin but also starch and water soluble carbohydrates. "Metabolites thereof" refers to the metabolic products of such fermentation products, for example as produced in the gastrointestinal tract or liver of the animal. Fermentation products and/or metabolites thereof which may be measured according to the methods of the invention include, but are not limited to: volatile fatty acids (VFAs), such as acetate, butyrate, propionate, or branched chain VFAs (including, for example, isobutyrate, isovalerate or 2-methylbutyrate); precursors to VFAs in bacterial fermentation, such as lactyl CoA, acryloyl CoA, propionyl CoA, pyruvate, acetyl CoA, acetyl phosphate, butyryl CoA, crotonyl CoA, ß-OH butyryl CoA; and metabolic products of VFAs, such as acetoacetate, ß-hydroxybutyrate, crotonyl CoA, L-ß-hydroxybutyryl CoA and D-ß-hydroxybutyryl CoA, lactate, propionyl CoA, acetyl CoA and malonyl CoA.

Animals of the genus *Equus* with lower weight loss propensity have a more diverse starting gut microbiome composition (as detailed below and demonstrated in the examples). Without wishing to be bound by theory, such animals may be more metabolically efficient, with a greater fermentative capacity, and thus greater uptake of fermentation products (such as VFAs) and/or metabolites thereof from the gastrointestinal tract into the circulation (thus increasing their concentration in blood coming from the gastrointestinal tract). As a consequence, or in addition, or alternatively, they may be better able to increase fibre digestibility when fed a fibre-restricted diet and thereby become more metabolically efficient during states of negative energy balance, compared to those losing more weight. This may limit the breakdown of triglyceride stores (and thus weight loss) during negative energy balance. Accordingly, in embodiments where blood or urine samples are assessed, the concentration of the one or more fermentation products and/or metabolites thereof that are assessed according to the invention (e.g. the one or more VFAs) may be negatively associated with the predicted weight loss of the animal.

Fermentation product and/or metabolite thereof concentrations may be measured in a sample obtained from the animal by any suitable means known in the art, for example gas liquid chromatography as carried out in the examples. Preferably, the sample is a faecal, blood or urine sample (more preferably a faecal sample), and an exemplary protocol for extracting fermentation products, such as VFAs, and/or metabolites thereof from faecal samples is provided in the examples. Determining the concentration of more than one different fermentation products and/or metabolites thereof (such as more than one different VFAs) for each sample, such as at least 2, 3, 4 or 5, may improve the predictive power of methods of the invention.

Preferably, the one or more fermentation products and/or metabolites thereof assessed in methods of the invention are one or more carbohydrate fermentation products, and more preferably one or more VFAs, as were analysed in the examples. More preferably, the one or more VFAs is selected from the group consisting of acetate, butyrate, propionate and or branched chain VFAs. As demonstrated in the examples, outset concentrations of these VFAs express strong positive correlations with weight loss (see FIG. 9). More preferably, the VFA is acetate, the outset concentration of which expresses the strongest positive correlation with weight loss of all VFAs analysed in the examples.

In an especially preferred embodiment, the acetate concentration in a sample obtained from the animal (preferably a faecal sample) is used to predict weight loss. A concentration of at least 10 mM acetate is indicative of acceptable weight loss propensity of the animal. Preferably, a concentration of at least 12 mM acetate is predictive of good weight loss propensity, such as between 12 mM and 20 mM, or between 12 mM and 15 mM. A concentration of above 20 mM acetate is predictive of very good weight loss propensity. For example, the inventors have shown that a concentration of at least 12 mM acetate is predictive of the loss of at least 8% outset body mass after a period of caloric restriction, preferably wherein the animal ingests a mean of less than 1.10% of its body mass in dry matter per day for at least 7 weeks. This concentration of acetate provides a test sensitivity of 88.9% and specificity of 100% for the prediction of good weight loss propensity as defined above. In another especially preferred embodiment, a concentration of at least 12 mM acetate is predictive of the loss of at least 1.14% outset body mass per week during caloric restriction, preferably wherein the animal ingests a mean of less than 1.10% of its body mass in dry matter per day.

In another preferred embodiment, a concentration of at least 20 mM acetate (such as between 20 and 25 mM acetate) is predictive of a high rate of weight loss, e.g. of at least 8.5% outset body mass after a period of caloric restriction; preferably wherein the animal ingests a mean of less than 1.10% of its body mass in dry matter per day for at least 7 weeks.

In other preferred embodiments, the propionate concentration in a sample obtained from the animal (preferably a faecal sample) is used to predict weight loss. For example, a concentration of at least 4.0 mM (such as between 4.0 mM and 6.0 mM) propionate is indicative of good weight loss propensity of the animal. In such embodiments, a concentration of (i) at least 4.0 mM (such as between 4.0 mM and 6.0 mM) propionate is predictive of loss of at least 7.5% outset body mass, and/or (ii) at least 5.0 mM (such as between 5.0 mM and 6.0 mM) propionate is predictive of loss of at least 8.0% outset body mass, after a period of caloric restriction. In other preferred embodiments, the butyrate concentration in a sample obtained from the animal (preferably a faecal sample) is used to predict weight loss. For example, a concentration of at least 1.5 mM (such as between 1.5 mM and 3.0 mM) butyrate is indicative of good weight loss propensity of the animal. In such embodiments, a concentration of (i) at least 1.5 mM (such as between 1.5 mM and 3.0 mM) butyrate is predictive of loss of at least 8.0% outset body mass, and/or (ii) at least 2.0 mM (such as between 2.0 mM and 3.0 mM) butyrate is predictive of loss of at least 8.5% outset body mass, and/or (iii) at least 2.5 mM (such as between 2.5 mM and 3.0 mM) butyrate is predictive of loss of at least 9.0% outset body mass, after a period of caloric restriction. In other preferred embodiments, the branched chain VFA concentration in a sample obtained from the animal (preferably a faecal sample) is used to predict weight loss. For example, a concentration of at least 1.0 mM (such as between 1.0 mM and 2.0 mM) branched chain VFAs is indicative of good weight loss propensity of the animal. In such embodiments, a concentration of (i) at least 1.0 mM (such as between 1.0 mM and 2.0 mM) branched chain VFAs may is predictive of loss of at least 7.5% outset body mass, and/or (ii) at least 1.5 mM (such as between 1.5 mM and 2.0 mM) branched chain VFAs is predictive of loss of at least 8.0% outset body mass, after a period of caloric restriction. In the above embodiments, said period of caloric restriction is preferably at least 7 weeks wherein the animal ingests a mean of less than 1.10% of its body mass in dry matter per day.

In other embodiments, ratios of the concentrations of different VFAs in the sample (preferably, a faecal sample) may be used as predictors of weight loss. For example, in another preferred embodiment, a ratio of total acetate plus butyrate concentration to propionate concentration in the sample of above 3.75:1, and preferably within the range of 3.79:1-4.95:1, is predictive of good weight loss propensity of the animal, such as the loss of at least 8.0% or at least 8.7% outset body mass after a period of caloric restriction, preferably wherein the animal ingests a mean of less than 1.10% of its body mass in dry matter per day for at least 7 weeks. In another preferred embodiment, a ratio of total acetate plus butyrate concentration to propionate concentration in the sample of above 3.75:1, and preferably within the range of 3.79:1-4.95:1, is predictive of the loss of at least 1.25% outset body mass per week during caloric restriction, preferably wherein the animal ingests a mean of less than 1.10% of its body mass in dry matter per day.

As the skilled person will appreciate, a lesser degree of caloric restriction over a longer period of time may be expected to yield similar levels of weight loss. Therefore, in the above embodiments (in which acetate, butyrate, propionate or branched chain VFA concentrations, or ratios thereof, are assessed), said period of caloric restriction may alternatively be defined as at least 8, 10, 12, 14 or 16 weeks or more, wherein for said periods the animal ingests a mean of less than 1.15%, 1.20%, 1.30%, 1.40%, or 1.50% respectively of its body mass in dry matter per day.

The concentrations of the fermentation product and/or metabolite thereof may be assessed as detailed above either alone or in combination with other predictors of weight loss (bacterial population diversity, abundance/relative abundance of bacterial *taxa*), as detailed below.

Bacterial Population Diversity as a Predictor of Weight Loss

According to another aspect of the invention, a diversity measure of the bacterial population in a sample obtained from an animal of the genus *Equus* is used as a predictor of weight loss, preferably weight loss in response to caloric restriction. As shown in the examples (see Example 1), various diversity measures are negatively associated with subsequent weight loss. "Negatively associated" means there exists a negative correlation between said diversity measure and subsequent weight loss (see FIG. 8 as an example) or, expressed differently, a lower diversity measure of the bacterial population in the sample is predictive of more subsequent weight loss than a higher diversity measure, and vice versa. Animals which show a higher diversity measure in the sample can generally be expected to lose weight slower compared to animals which have a lower diversity measure (when the same measure is assessed), on an equivalent diet. In addition or alternatively, animals with a higher diversity measure can be expected to lose less weight in the same time span compared to animals with a lower diversity measure (when the same measure is assessed), on an equivalent diet.

Bacterial population diversity measures may be calculated by methods comprising DNA sequencing, RNA sequencing, protein sequence homology or the use of other biological markers indicative of a bacterial species. Preferably, DNA sequencing is used, and more preferably 16s rDNA sequencing, as performed in the examples. For example, genomic DNA may be extracted from samples and amplified by quantitative PCR (qPCR) using 16s rDNA specific primers to create a DNA library which can then be sequenced, as carried out in the examples. Sequence data obtained from the libraries then allows for the calculation of diversity measures. Exemplary 16s rDNA specific primers (as were used in the examples) are as follows:

Forward primer: AGAGTTTGATCCTGGCTCAG (SEQ ID NO: 1)

Reverse primer: ACGAGTGCGTCTGCTGCC-TYCCGTA (SEQ ID NO: 2)

In preferred embodiments, the diversity measure of the bacterial population in the sample (preferably, a faecal sample) calculated is Inverse Simpson diversity, Shannon-Weiner diversity, or the number of different bacterial species in the sample (also referred to as the number of observed species, or S.obs). As shown in the examples, these diversity measures express negative correlations with subsequent weight loss (see FIG. 8). Combinations of different diversity measures (preferably those listed above), may also be used to improve the accuracy of the prediction. For example, an Inverse Simson diversity of less than 70, preferably less than 45 (such as between 10 and 70, preferably between 10 and 45), a Shannon-Weiner diversity of less than 6.0, preferably less than 5.3 (such as between 4.0 and 6.0, preferably between 4.0 and 5.3) and a number of observed species of less than 1900, preferably less than 1700 (such as between 1000 and 1900, preferably between 1000 and 1700) are all indicative of good weight loss propensity of the animal.

Calculation of more than one different diversity measure for each sample, such as two or three such measures, may improve the predictive power of methods of the invention.

Inverse Simpson diversity is calculated according to formula (I):

$$1/\Sigma pi^2, \text{ wherein Pi is the proportion of individuals belonging to species } i \tag{I}$$

In a preferred embodiment, a calculated Inverse Simpson diversity of less than (in increasing preference) 75, 70, 65, 60, 55, 50, 45, 40, 35 or 30 (such as between 10 and 70), is predictive of loss of at least 8% outset body mass after a period of caloric restriction (or loss of at least 1.14% body mass per week during the period of caloric restriction); preferably, less than 45, 40, 35 or 30 (such as between 10 and 45), more preferably less than 30 (such as between 10 and 30), is predictive of loss at least 8.7% outset body mass after a period of caloric restriction (or loss of at least 1.25% body mass per week during the period of caloric restriction).

Shannon-Weiner diversity is calculated according to formula (II):

$$-\Sigma Pi \ln(Pi), \text{ wherein Pi is the proportion of individuals belonging to species } i \tag{II}$$

In another preferred embodiment, a calculated Shannon-Weiner diversity of less than (in increasing preference) 6.0, 5.9, 5.8, 5.7, 5.6, 5.5, 5.4, 5.3, 5.2, 5.1 or 5.0 (such as between 4.0 and 6.0), is predictive of loss of at least 8% outset body mass after a period of caloric restriction (or loss of at least 1.14% body mass per week during the period of caloric restriction); preferably, less than 5.3, 5.2, 5.1 or 5.0 (such as between 4.0 and 5.3), more preferably less than 5.0 (such as between 4.0 and 5.0) is predictive of loss of at least 8.7% outset body mass after a period of caloric restriction (or loss of at least 1.25% body mass per week during the period of caloric restriction).

In another preferred embodiment, the number of different bacterial species present in the sample may be calculated, and the presence of less than (in increasing preference) 1900, 1850, 1800, 1750, 1700, 1650, 1600, 1550 (such as between 1000 and 1900), is predictive of loss of at least 8% outset body mass after a period of caloric restriction (or loss of at least 1.14% body mass per week during the period of caloric restriction); preferably, less than 1700, 1600, 1550 or 1500 (such as between 1000 and 1700), more preferably less than 1500 (such as between 1000 and 1500) different bacterial species, is predictive of loss of at least 8.7% outset body mass after a period of caloric restriction (or loss of at least 1.25% body mass per week during the period of caloric restriction).

In the above embodiments, the period of caloric restriction is preferably at least 7 weeks wherein the animal ingests a mean of less than 1.10% of its body mass in dry matter per day.

In other preferred embodiments, a calculated Inverse Simpson diversity of (i) less than 100 (such as between 10 and 100) is predictive of loss of at least 7.5% outset body mass, and/or (ii) less than 50 (such as between 10 and 50) is predictive of loss of at least 8.0% outset body mass after a period of caloric restriction. In other preferred embodiments, a calculated Shannon-Weiner diversity of (i) less than 6.0 (such as between 4.0 and 6.0) is predictive of loss of at least 7.0% outset body mass, and/or (ii) less than 5.5 (such as between 4.0 and 5.5) is predictive of loss of at least 8.0% outset body mass, and/or (iii) less than 5.0 (such as between 4.0 and 5.0) is predictive of loss of at least 9.5% outset body mass after a period of caloric restriction. In other preferred embodiments, a calculated number of different bacterial species of (i) less than 1800 (such as between 1000-1800) is predictive of loss of at least 8.0% outset body mass, and/or (ii) less than 1600 (such as between 1000-1600) is predictive of loss of at least 8.5% outset body mass, and/or (iii) less than 1400 (such as between 1000-1400) is predictive of loss of at least 9.0% outset body mass after a period of caloric restriction. In the above embodiments, said period of caloric restriction is preferably at least 7 weeks wherein the animal ingests a mean of less than 1.10% of its body mass in dry matter per day.

In the above embodiments (where Inverse Simpson diversity, Shannon-Weiner diversity, or the number of observed species are assessed), said period of caloric restriction may alternatively be defined as at least 8, 10, 12, 14 or 16 weeks or more, wherein for said periods the animal ingests a mean of less than 1.10%, 1.20%, 1.30%, 1.40%, or 1.50% respectively of its body mass in dry matter per day.

Bacterial population diversity measures may be used as detailed above either alone or in combination with other predictors of weight loss (fermentation product or metabolite thereof concentrations, and/or abundance/relative abundance of bacterial *taxa*), as detailed above and below.

Abundance/Relative Abundance of Bacteria as a Predictor of Weight Loss

According to another aspect of the invention, the abundance and/or relative abundance of: (i) bacteria of the genus Sphaerochaeta, and/or (ii) bacteria of the genus *Treponema*, and/or (iii) bacteria of the genus *Anaerovorax*, and/or (iv) bacteria of the genus *Mobilitalea*, and/or (v) bacteria of the phylum Actinobacteria, and/or (vi) bacteria of the phylum Spirochaetes, and/or (vi) fibre-fermenting bacteria (such as bacteria of the genus *fibrobacter*), is/are used as a predictor of weight loss, preferably weight loss in response to caloric restriction. As shown in the examples, the abundance/relative abundance of such bacteria is negatively associated with subsequent weight loss. "Negatively associated" is used as defined above in relation to bacterial population diversity. Bacterial abundance and/or relative abundance may be calculated by the methods detailed above in relation to bacterial population diversity measures. Calculation of the abundance and/or relative abundance or more than one of the above bacteria (defined as (i) to (vii), above) for each sample and/or animal, such as 2, 3, 4, 5, 6 or 7 such bacteria, may improve the predictive power of methods of the invention. Preferably, the abundance and/or relative abundance of: (i) bacteria of the genus Sphaerochaeta, and/or (ii) bacteria of the genus *Treponema*, and/or (iii) bacteria of the genus *Anaerovorax* and/or (iv) bacteria of the genus *Mobilitalea*, and/or (v) bacteria of the phylum Actinobacteria, and/or (vi) bacteria of the phylum Spirochaetes is/are used as a predictor of weight loss.

In a preferred embodiment, an abundance of bacteria of the genus Sphaerochaeta in the sample of less than login 2.5 counts (such as between login 1.0 and login 2.5 counts), and/or a relative abundance of less than 0.05%, is predictive of good weight loss propensity of the animal; for example, loss of at least 8% outset body mass after a period of caloric restriction.

In another preferred embodiment, an abundance of bacteria of the genus *Mobilitalea* in the sample of less than $\log_{10}$ 2.5 counts, preferably less than $\log_{10}$ 1.6 counts (such as between $\log_{10}$ 0.5 and $\log_{10}$ 2.5 counts, preferably between $\log_{10}$ 0.5 and $\log_{10}$ 1.6 counts), and/or a relative abundance of less than 0.03%, is predictive of good weight loss propensity of the animal; for example, loss of at least 8.0%, preferably at least 8.7%, outset body mass after a period of caloric restriction; or loss of at least 1.14%, preferably at least 1.25%, body mass per week during the period of caloric restriction.

In another preferred embodiment, a relative abundance of bacteria of the genus *Treponema* in the sample of less than 1.7% is predictive of good weight loss propensity of the animal; for example, loss of at least 8% outset body mass after a period of caloric restriction.

In another preferred embodiment, a relative abundance of bacteria of the genus *Anaerovorax* in the sample of less than 0.11% is predictive of good weight loss propensity of the animal; for example, loss of at least 8% outset body mass after a period of caloric restriction.

In another preferred embodiment, an abundance of bacteria of the phylum Actinobacteria in the sample of less than $\log_{10}$ 3.7 counts, preferably less than $\log_{10}$ 2.5 counts (such as between $\log_{10}$ 2.0 and $\log_{10}$ 3.7 counts, preferably between $\log_{10}$ 2.5 and $\log_{10}$ 3.7 counts) is predictive of good weight loss propensity of the animal; for example, loss of at least 8.0%, preferably at least 8.7%, outset body mass after a period of caloric restriction; or loss of at least 1.14%, preferably at least 1.25%, body mass per week during the period of caloric restriction.

In another preferred embodiment, a relative abundance of bacteria of the phylum Spirochaetes in the sample of less than 2.3% is predictive of good weight loss propensity of the animal; for example, loss of at least 8% outset body mass after a period of caloric restriction.

In some embodiments, calculation of the abundance of fibre-fermenting bacteria (in addition to the above bacterial *taxa*) may further improve the predictive power of methods of the invention. Alternatively, in some embodiments, calculation of the abundance of fibre-fermenting bacteria is used as a predictor of weight loss (in and of itself). In such embodiments, where the abundance and/or relative abundance of fibre-fermenting bacteria is assessed, the abundance of bacteria of the genus *Fibrobacter* in the sample may be calculated, wherein the abundance(s) of said fibre-fermenting bacteria is/are negatively associated with predicted weight loss.

In the above embodiments (where Sphaerochaeta, *Mobilitalea, Treponema, Anaerovorax*, Actinobacteria, Spirochaetes and fibre-fermenting bacteria abundance and/or relative abundance are assessed), said period of caloric restriction is preferably at least 7 weeks, wherein the animal ingests a mean of less than 1.10% of its body mass in dry matter per day. Said period of caloric restriction may alternatively be defined as at least 8, 10, 12, 14 or 16 weeks, wherein for said periods the animal ingests a mean of less than 1.10%, 1.20%, 1.30%, 1.40%, or 1.50% respectively of its body mass in dry matter per day.

The abundance and/or relative abundance of the above bacteria may be used as detailed above either alone or in combination with other predictors of weight loss (fermentation product concentrations and/or bacterial population diversity measures), as detailed above.

The Sample

The methods of the invention use a faecal sample, blood sample, urine sample or a sample from the gastrointestinal lumen of the animal of the genus *Equus*. Faecal and urine samples are convenient because their collection is non-invasive and it also allows for easy repeated sampling of individuals over a period of time, and are the preferred samples used in methods of the invention. Faecal samples, as were analysed in the examples, are especially preferred samples used in methods of the invention. The invention can also be used with other samples, such as ileal, jejunal, duodenal samples and colonic samples. In some embodiments, the sample used in methods of the invention is not a blood or urine sample.

The sample may be a fresh sample. The sample may also be frozen or stabilised by other means such as addition to preservation buffers or by dehydration using methods such as freeze drying before use in the methods of the invention.

Before use in the methods of the invention (other than fermentation product and/or metabolite thereof concentration assessment), the sample will generally be processed to extract DNA. Methods for isolating DNA are well known in the art, as reviewed in[21], for example. Suitable methods include, for instance, the QIAamp Power Faecal DNA kit (Qiagen).

In methods of the invention, predictors of weight loss may be assessed from a single sample, or, for greater accuracy, mean values from a plurality of samples, such as 2, 3, 4 or 5 or more samples from the same animal may be assessed as a predictor of weight loss.

General

The practice of the present invention will employ, unless otherwise indicated, conventional methods of chemistry, biochemistry, molecular biology, immunology and pharmacology, within the skill of the art. Such techniques are explained fully in the literature[22-29].

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of reference 30. A preferred alignment is determined using the BLAST (basic local alignment search tool) algorithm or the Smith-Waterman homology search algorithm[31] using an affine gap search with a gap open penalty of 12 and a gap extension penalty of 2, BLOSUM matrix of 62. The Smith-Waterman homology search algorithm is disclosed in reference 31. The alignment may be over the entire reference sequence, i.e. it may be over 100% length of the sequences disclosed herein.

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Materials and Methods

Animals and Husbandry

Sixteen obese (BCS >7/9), Welsh Mountain (Section A) pony mares (n=8 Year 1; n=8 Year 2), were studied over an 11-week period (December-February; Table S2). The animals were loaned to the study by local pony breeders within a 30-mile radius of the University of Liverpool's, Ness Heath Farm. All animals were clinically examined at the point of recruitment, had no signs of overt disease and were considered to be in good overall health. Routine foot care and vaccination protocols were maintained throughout the study. Animals were individually housed in (3 m×5 m) loose boxes within the same barn, bedded on wood shavings and had free access to fresh water at all times. When possible, ponies were given access to pasture for 30 minutes daily to permit basal exercise and social contact. To ensure total control over nutrition which was provided within the stables, pasture intake while at exercise was prevented using closed grazing muzzles (Shires).

All procedures were conducted in accordance with Home Office requirements, approved by the University of Liverpool's, Animal Welfare Committee. Written informed consent was obtained from all owners.

Study Design

This 11-week study was designed to allow the evaluation of any associations between weight loss responsiveness and changes in the gastro-intestinal microbiome during a 7-week period of dietary restriction. Animals were maintained on a grass hay diet (same batch across both years) throughout.

Prior to the initiation of negative energy balance, animals first underwent a 4-week period of adaptation to the study diet and husbandry conditions. During this 4-week 'pre-diet' period, individual animals were offered grass hay at 2% of their outset BM as DM daily, a plane of nutrition estimated to approximate maintenance in terms of digestible energy (DE) and crude protein (CP) content. To mimic standard husbandry practices, daily hay allowances for each animal were equally divided and offered as two daily meals (08.30 h and 16.30 h). To ensure adequacy of vitamin and mineral intakes, a moistened nutrient balancer product (Spillers Lite) was fed daily (08.30 h, 0.1% BM as DM). Mean compositions for key nutrients were: Hay; Gross energy (GE), 18.9 MJ/kg DM, Ash, 4.0%, Crude Protein (CP) 8.1%, Acid detergent fibre (ADF), 41.2%, Neutral detergent fibre (NDF) 64.7%, starch. 0.6%, water soluble carbohydrates (WSC) 15.6%. Vitamin/mineral balancer; GE 16.35 MJ/kg DM, DE, 9.5 MJ/kg DM, Ash, 14.0%, CP 21.1%, ADF, 14.3%, NDF, 31.7%, starch, 10.5, WSC 12.5%. Samples of hay and balancer were analysed prior to the 4-week pre-diet phase in both years and there was no difference in the composition of key nutrients between years. For the remaining seven weeks of the study, hay intake was restricted to 1% BM as DM daily with 0.1% BM as a nutrient balancer meal. This degree of negative energy balance was predicted to induce a mean weight loss of 1% of outset BM weekly. Meals were offered as previously described. Individual feed provisions were recalculated weekly during this period to account for changes in BM.

Physical Measurements

Each week, BM was recorded (to nearest 500 g) between 08.30 h and 09.00 h (regularly calibrated weighbridge: Lightweight Intermediate; Horseweigh). BCS was recorded for each animal using the Kohnke (1992) modification of the Henneke et al. (1983) system, by the same individual throughout the duration of the study.

Faecal Collection

Samples of faeces were collected weekly from each animal within 5 minutes of spontaneous voiding (first defecation spontaneously voided after 09.00) throughout the 11-week study. Additionally, faecal samples were also collected across the final 3 consecutive days of the 2% hay feeding, 'pre-diet' period and again during the final three consecutive days of dietary restriction. Fresh faecal samples were collected from the bedding/floor area with a gloved hand into a clean steel bowl to minimise environmental contamination, hand-mixed and aliquoted into four, 5 ml sterile vials (Scientific Laboratory Supplies, UK). Vials were snap-frozen in liquid nitrogen and stored at −80° C. prior to DNA extraction.

Estimates of Total Body Composition

Total body water (TBW) and total body fat mass were calculated twice for each individual animal; once during the final week of the 'pre-diet' phase and during the final week of the dietary restriction phase, using the deuterium oxide (D20) dilution method, as previously described and validated for clinical use in the pony[32]. Deuterium enrichments in plasma samples were analysed in duplicate by a commercial laboratory (Iso-analytical, Cheshire, UK) by gas isotope ratio mass spectrometry.

Combined Glucose-Insulin Tolerance Test (CGIT)

A dynamic CGIT test was performed twice for each individual animal; once during the final week of the 'pre-diet' phase and during the final week of the dietary restriction[15]. Blood samples were immediately transferred to lithium heparinised tubes (BD vacutainer), mixed and placed on ice prior to centrifugation (2000 g for 10 minutes). Plasma was aliquoted in duplicate and stored at −20° C. prior to analysis. Plasma glucose samples were analysed using the hexokinase method. Plasma insulin concentrations were measured using a chemiluminescent assay (Siemens Immulite 1000R, Chemiluminescent Assay).

Apparent Digestibility

Digestibility trials were conducted twice for individual ponies by total faecal collection over 3 consecutive days (72 hour) once during the final week of the 'pre-diet' phase and again during the final week of the dietary restriction. Any refused feed was recorded at the end of each 24-hour period. Total daily faecal collections were weighed, thoroughly mixed and duplicate samples were collected for analysis. Dry matter (DM) contents of faeces were determined by drying (70° C.) duplicate samples (~250 g) to constant mass. Ash contents were recorded following combustion of duplicate DM samples at 550° C. (Carbolite OAF:1; Carbolite Furnaces). The three dry faecal samples collected over a 72-hour period were ground, pooled and homogenized for the evaluation of GE content (MJ/kgDM) by bomb calorimetry at a commercial laboratory (Sciantec, UK). Additionally, the fibre content (ADF and NDF) of the dried faecal samples was measured by wet chemistry at a commercial laboratory (Dairy One, Ithaca, USA).

DNA Extraction and Quantitative PCR

Genomic DNA was extracted from freeze-dried faecal samples (25 mg DM) which were bead-beaten in 4% SDS lysis buffer for 45 s. DNA was extracted using a CTAB/ Chloroform method (adapted from reference 33). Concentrations and qualities of genomic DNA were assessed by spectrophotometry (Nanodrop ND-100, Thermo Scientific, USA). Absolute concentrations of DNA from total bacteria, protozoa and fungi were determined by qPCR and serial dilutions of their respective standards (10' to $10^5$) as previously described[34,35]. Quantitative PCR (qPCR) was conducted in triplicate using a LightCycler 480 System (Roche, Mannheim, Germany).

Ion Torrent Next Generation Sequencing

Bacterial communities were studied using Next Generation Sequencing (NGS)[36]. For bacterial profiling, amplification of the V1-V2 hypervariable regions of the 16S rRNA was carried out using bacterial primers (27F and 357R) followed by Ion Torrent adaptors. Forward primers were barcoded with 10 nucleotides to allow sample identification. PCR was carried out in a 25 μL reaction vessel containing DNA template (1 μL), 0.2 μL reverse primer, 1 μL forward primer, 5 μL buffer (PCR Biosystems Ltd., London, UK), 0.25 μL bio HiFi polymerase (PCR Biosystems) and 17.6 μL molecular grade water. Amplification conditions for bacteria and methanogens were 95° C. for 1 min, then 22 cycles of 95° C. for 15 s, 55° C. for 15 s and 72° C. for 30 s. To assess the quality of amplifications, resultant amplicons were visualized on a 1% agarose gel. PCR products were then purified using Agencourt AMpure XP beads (Beckman Coulter Inc., Fullerton, USA) and DNA concentration was determined using an Epoch Microplate Spectrophotometer fitted with a Take 3 Micro-Volume plate (BioTek, Potton, UK) to enable equimolar pooling of samples with unique barcodes.

Libraries were further purified using the EGel system with 2% agarose gel (Life Technologies Ltd., Paisley, UK). Purified libraries were assessed for quality and quantified on an Agilent 2100 Bioanalyzer with High Sensitivity DNA chip (Agilent Technologies Ltd., Stockport, UK). Library preparation for NGS sequencing was carried out using the Ion Chef system (Life Technologies UK Ltd) and the Ion PGM HiQ Chef kit, and sequencing using the Ion Torrent Personal Genome Machine (PGM) system on an Ion PGM Sequencing 316 Chips v2 BC.

Following sequencing, data were processed as previously described[36]. Briefly, sample identification numbers were assigned to multiplexed reads using the MOTHUR software environment. Data were denoised by removing low-quality sequences, sequencing errors and chimeras (quality parameters: maximum 10 homopolymers, qaverage 13, qwindow 25, for archaea the qwindow was set at 30, and erate=1; Chimera check, both de novo and database driven using Uchime). Sequences were clustered into OTUSs using the Uparse pipeline at 97% identity. Bacterial taxonomic information on 16S rRNA sequences was obtained by comparing against Ribosomal Database Project-I[37]. The number of reads per sample were normalised to the sample with the lowest number of sequences.

Volatile Fatty Acid Measurement

Faecal samples were defrosted and diluted 1:5 w/v with distilled $H_2O$ (2 g sample/8 mL $H_2O$) to make a faecal slurry and pH was recorded prior to the addition of 20% ortho-phosphoric acid (containing 20 mM 2-ethyl butyric acid as an internal standard) also at 1:5 (1 mL acid/4 mL faecal slurry) to deproteinise the samples. For VFA analyses, slurries were left for 24 h to allow sediments to settle before being syringe-filtered through a glass-fibre pre-filter (0.7 μm pore, Millipore) and a nitrocellulose membrane (0.45 μm pore; Millipore) into a glass vial and capped. VFAs were determined by gas liquid chromatography using ethyl butyric acid as the internal standard as described in reference 38.

Statistical Analysis

Phenotype Data

All data was inputted into Excel and exported for statistical analysis into STATA 13.1 (Statacorp, Tex.). The pattern of weight change during the weight-loss phase of the study was investigated by fitting a mixed effects regression model with body mass (kg) as the outcome variable. Outset body mass (Week 0) was included to account for differences between individual animals in outset BM. Time (week) was added as an explanatory variable and polynomial terms were fitted if they improved model fit as judged by the likelihood ratio test. Pony identity was included as a random intercept with time as a random slope. An unstructured covariance matrix was employed for the random effects. Body mass was predicted from the model and using this, a proportional weight loss (adjusted to Week 0) was calculated and used to rank animals according to weight-loss. This was then divided into terciles (high (8.77, 9.17, 11.32 and 11.59% outset body mass lost), mid (7.97, 8.15, 8.42, 8.45 and 8.62% outset body mass lost) and low (7.11, 7.22, 7.53, 7.94 and 7.94% outset body mass lost) weight-loss) to enable further interrogation of the data. Wilcoxon sign-rank test was employed to evaluate differences in digestibility, body composition and glucose/insulin dynamics between pre- and post-diet measurements.

Diversity and Faecal VFA Analysis

Diversity indices (Inverse Simpson's and Shannon-Wiener), species observed (S.obs) and estimated species richness (S.Chao1) were calculated for all faecal samples at all time points using normalized data as recommended to reduce over-inflation of true diversity in pyrosequencing data sets[39]. Data were assessed for normality visually adopting the "ladder of powers" approach. Transformations were performed where appropriate. Student t tests were performed to assess mean changes in VFA concentrations and diversity indices between the pre-diet and post-diet period (using arithmetic mean of final 3 days of pre-diet and post-diet samples). One-way ANOVA (Genstat® 12th edition; VSN International ltd.) was employed to assess differences in outset diversity and faecal VFA concentrations between weight-loss groups (high, mid, low), using Bonferroni-adjusted P value to correct for multiple testing. P-values were considered significant if <0.05. Findings were confirmed by univariate analysis (STATA 13.1, Statcorp, Tex.) whereby outset diversity or faecal VFA concentration was the explanatory variable and overall proportion weight-loss (logit transformed) was the outcome variable. In order to investigate further the ability of outset acetate concentration to predict the weight-loss success of an animal, a binary (yes/no) variable was generated whereby weight-loss success was defined as total percentage weight-loss of ≥8%. This value was selected on the basis of data collected within the current study. A receiver operating characteristic (ROC) curve was generated for outset acetate concentration as a predictor of weight-loss (yes/no). This allowed investigation of the optimal cut-off score for outset acetate concentration and generated sensitivity and specificity parameters. Additionally, analysis of composition of microbiomes (ANCOM) was employed using an R-implemented version 1.1-367 to evaluate if the outset abundance of any individual genera were significantly different between outset acetate concentrations (divided in quartiles).

Phylum and genera level differences in the microbiome following weight-loss were investigated by ANOVA (Genstat® 12th edition; VSN International ltd.). Statistical analyses excluded those for which an abundance of less than 0.05% was recorded. P values were adjusted for multiple testing using the method proposed by Benjamini and Hochberg[40] to decrease the false discovery rate. Findings with P<0.10 when applying Benjamini and Hochberg (1995) correction were regarded as statistically significant. ANCOM was employed to evaluate differences in the abundances of individual phyla/genera between weight-loss groups.

Differential abundances at an OTU level were evaluated using the bioconductor package DESEQ21 in the statistical package R, a methodology appropriate for the interrogation of high-throughput, sequencing count data, allowing models to be built using a negative binomial distribution to account for the distribution of read counts from each OTU[41].

Permutation multivariate analysis of variance (PERMANOVA) was used to determine overall significant differences in bacterial communities. Analyses were performed in PRIMER 6 & PERMANOVA+(versions 6.1.18 and 1.0.8 respectively; Primer-E, Ivybridge, UK). Abundance percentage data were subjected to square-root transformation and Bray-Curtis distance matrices were calculated. PERMANOVA was carried out using default settings with 9999 unrestricted permutations and the Monte Carlo P value was calculated. Analyses of Similarity (ANOSIM) were conducted in PRIMER 6 & PERMANOVA+, using the Bray-Curtis distance matrix calculated above. This analysis was used to provide a metric of the degree of divergence between communities, as given by the R statistic.

To calculate the contribution of environmental data on bacterial communities, distance-based linear modelling was used to calculate which environmental variables had a significant correlation with the community data. Significant variables were used in distance-based redundancy analysis (dbRDA)[42] as implemented in PRIMER 6 and PERMANOVA+.

Example 1—Coverage, Diversity and Volatile Fatty Acids

Figure 6:
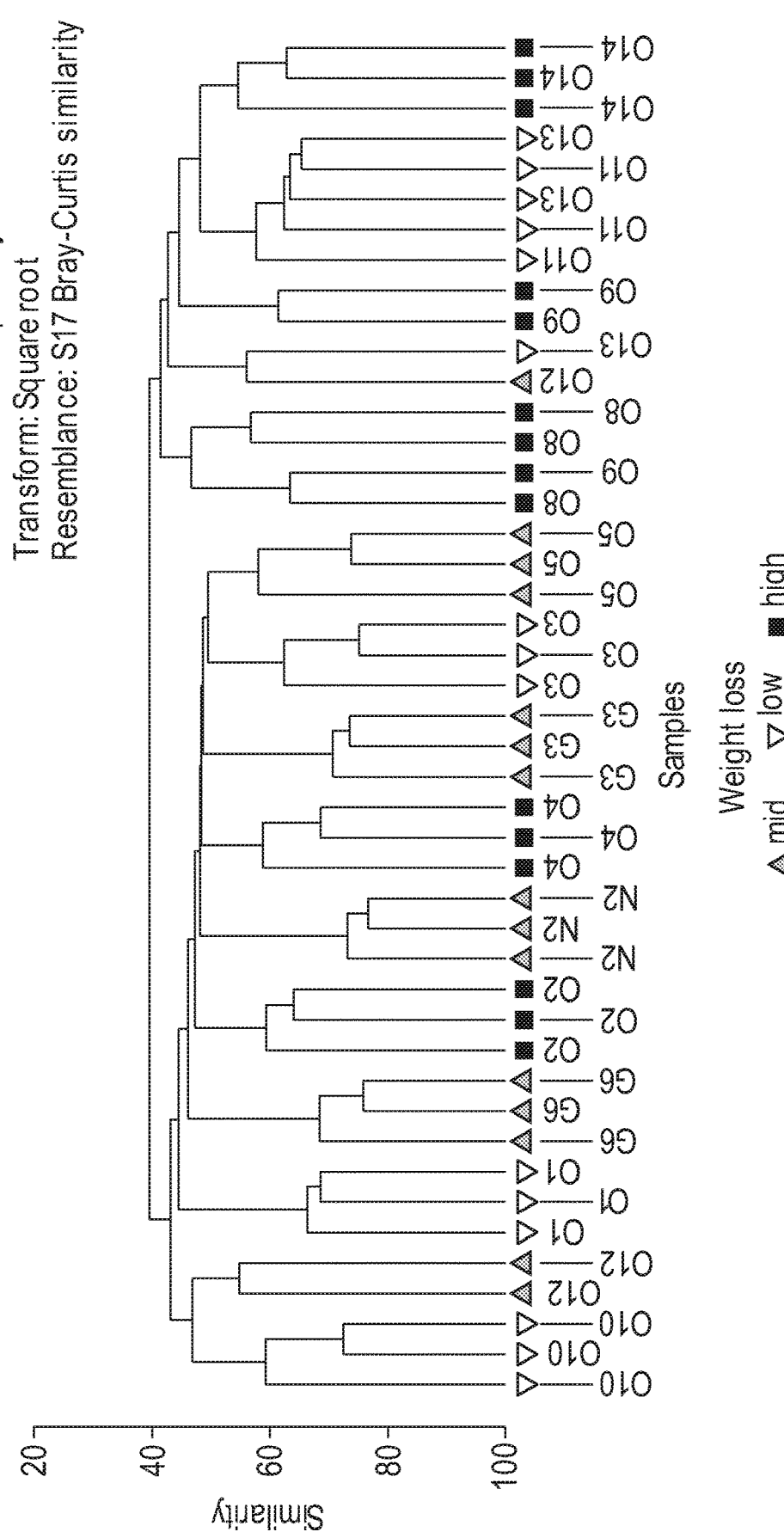
FIG. 6. Phylogenetic tree depicting clustering of the faecal bacterial microbiome within animal (n=15).
Figure 7:
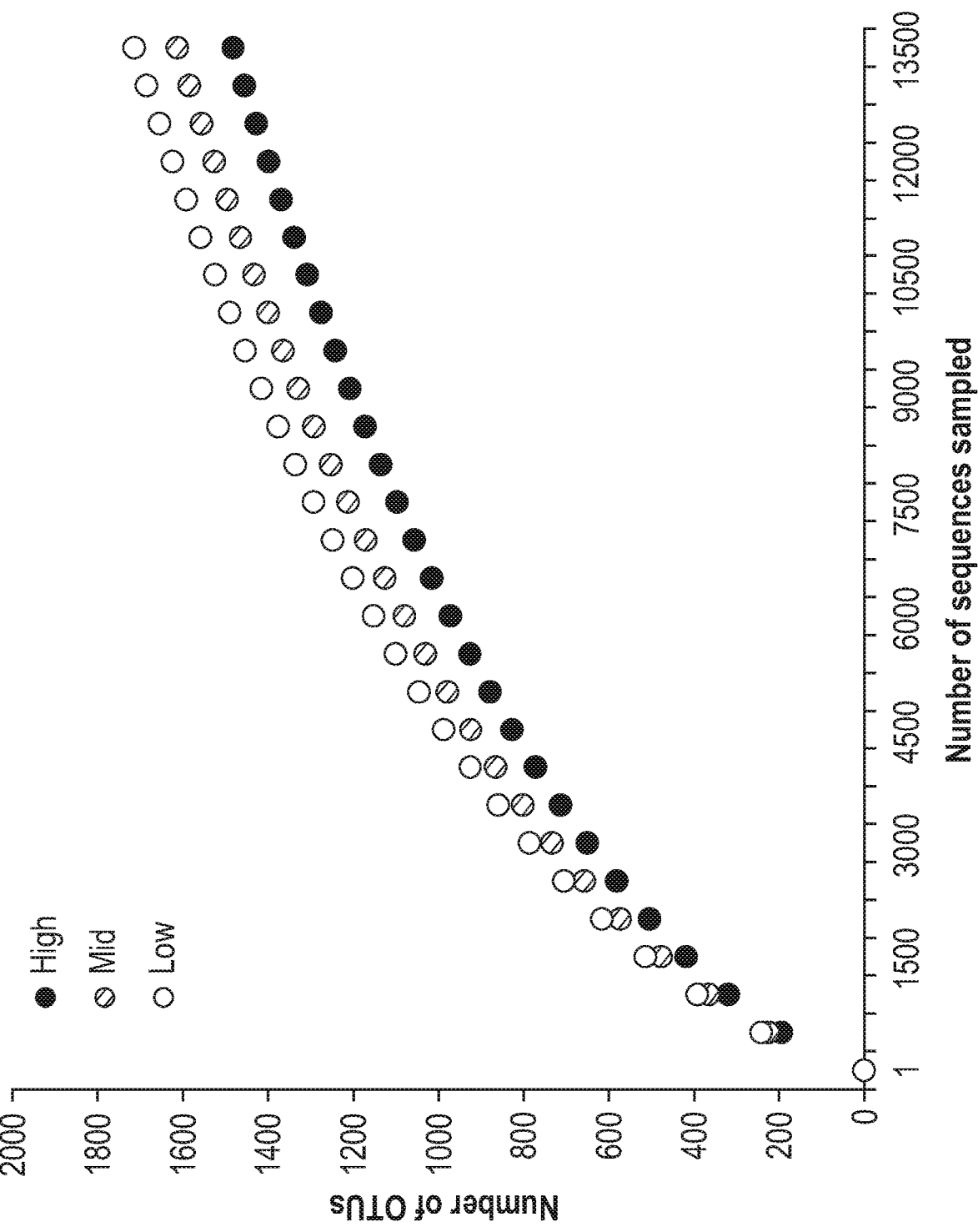
FIG. 7. Rarefaction curves.

Quality filtering of 16S rDNA amplicon sequences resulted in 16,028,420 high-quality sequences (320 bp long) which clustered in 9,536 different OTUs. A phylogenetic tree was constructed (PRIMER 6 with Bray Curtis dissimilarity, FIG. 6), which indicated that samples from an animal, collected on each of the three successive sampling days pre- and post-diet, tended to cluster together. This observation allowed data arising from these serial samples to be pooled for each animal. Pooled analyses provided 14,500 sequences per animal, per period after normalization. Rarefaction curves (FIG. 7) demonstrated that sample curves had not plateaued; indicating that complete sampling of these environments had not yet been achieved.

There were significant (p<0.05) reductions in Inverse Simpson, Shannon-Wiener, and S.obs measures of alpha diversity following weight-loss, but no differences were observed for Chao1 (Table 1). Furthermore, there were significant differences in outset (mean of 3 pre-diet days) measures of diversity (Inverse Simpson, Shannon-Wiener, and S.obs) between the three weight-loss groups (Table 1). This was confirmed by univariate regression analysis, whereby significant negative associations were identified between outset diversity measures and subsequent weight-loss (Table 3 and FIG. 8).

There were significant reductions in the concentration of acetate, butyrate, propionate and branched chain volatile fatty acids following weight-loss, however faecal pH remained unchanged (Table 2). There were no differences in the ratio of acetate plus butyrate to propionate between the pre-diet and post-diet samples, however the outset ratio (mean of 3 pre-diet samples) was greatest in the high weight-loss group compared to the low weight-loss group (4.37±0.58 vs. 3.24±0.50; p=0.04). Additionally, strong positive associations were identified between outset VFA concentrations and subsequent weight-loss (Acetate, $R^2$=0.52, p<0.01; Butyrate, $R^2$=0.34, p=0.02; Propionate, $R^2$=0.33, p=0.03; Table 4 and FIG. 9).

Figures 10, 11:
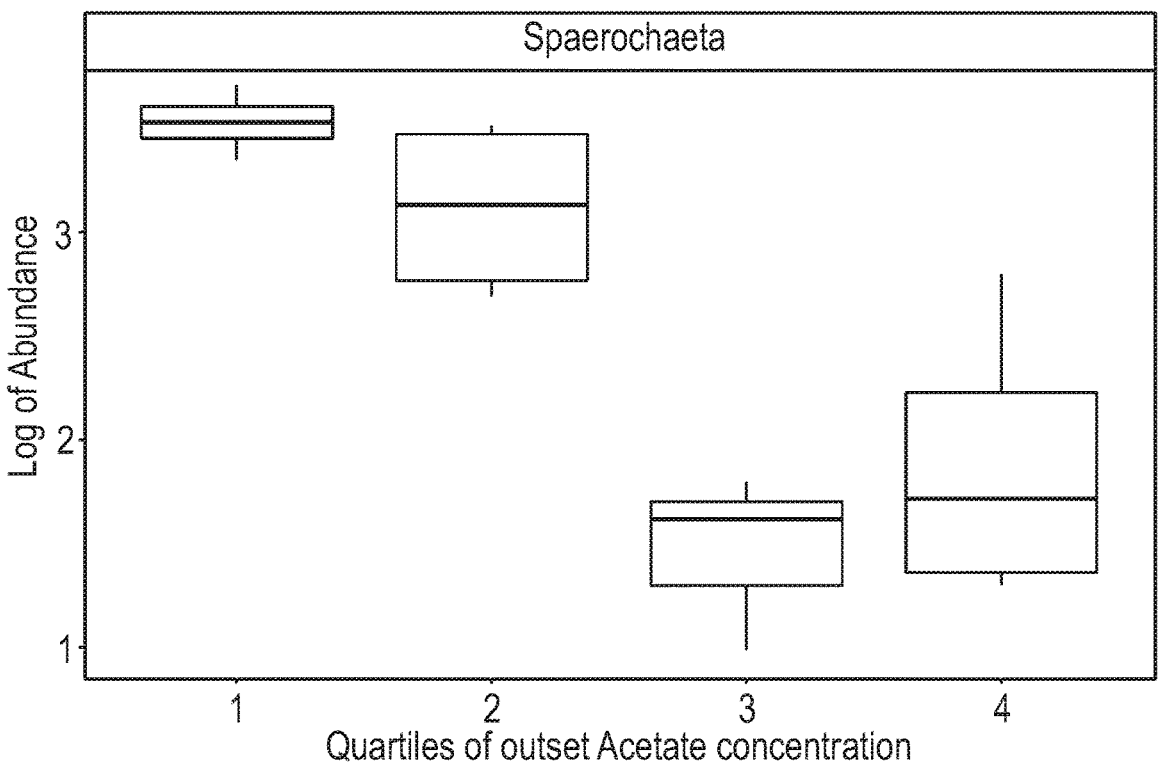
FIG. 10. Receiver operating characteristic (ROC) curve for outset acetate concentration as a predictor of animals achieving ≥8% weight-loss. At the optimal cut-off of 12 mM acetate, sensitivity was 88.9%, while specificity was 100%.
FIG. 11. The outset abundance of Spharerochaeta across quartiles of outset acetate concentration (1=low concentration; 4=high concentration) following ANCOM analysis. n=15.

Due to the significant association between outset acetate and subsequent weight-loss, a logistic regression model was fitted with the binary outcome of "weight loss>=8% BM". This was used to construct a receiver operating characteristic (ROC) curve to determine the ability of outset acetate concentration to predict subsequent weight-loss success (using target weight-loss of 8% outset body mass) and resulted in an area under the curve of 0.91 (FIG. 10). Optimal test performance achieved with the current data provided a cut-off value of 12 mM acetate which gave a test sensitivity of 88.9% (95% confidence intervals: 51.8-99.7) and specificity of 100% (95% confidence intervals: 54.1-100.0) for prediction of weight loss greater than 8%. ANCOM was then used to investigate associations between the outset abundance of any specific genera and outset acetate concentration (divided into quartiles). The outset abundance of Sphaerochaeta, Treponema, (both belonging to the Spirochaetes phyla), Anaerovorax and Mobilitalea (both belonging to Firmicutes phyla) were found to be significantly associated with outset acetate concentration (FIG. 11 and Table 5), whereby the outset abundance of the individual genera were greatest for those animals in the lowest quartile of outset acetate concentration.

TABLE 1

Diversity indices (mean ± SD) before (pre-diet), and following 7 weeks of dietary
restriction (post-diet; n = 15), and outset diversity indices (mean of 3 pre-
diet days ± SD) in the high (n = 5), medium (n = 5) and low (n = 5) weight-loss groups.

| Diversity measure | Pre-diet | Post-diet | P-value | High weight-loss group | Medium weight-loss group | Low weight-loss group | P-value |
|---|---|---|---|---|---|---|---|
| Inverse Simpson | 62.02 ± 47.66 | 27.03 ± 16.91 | <0.01 | 28.31 ± 13.14 | 54.10 ± 21.77 | 103.65 ± 60.32 | 0.03 |
| Shannon-Weiner | 5.46 ± 0.52 | 4.92 ± 0.54 | <0.01 | 4.94 ± 0.28 | 5.55 ± 0.35 | 5.95 ± 0.29 | <0.01 |
| S.Obs | 1717.33 ± 222.51 | 1576.20 ± 153.13 | 0.04 | 1488.93 ± 106.99 | 1748.27 ± 156.16 | 1914.80 ± 149.37 | <0.01 |
| S.Chaol | 2871.63 ± 401.75 | 2729.61 ± 324.73 | 0.37 | 2619.25 ± 279.27 | 2986.81 ± 552.08 | 3008.82 ± 249.78 | 0.24 |

TABLE 2 pH and volatile fatty acid concentrations (mean ± SD)
before (pre-diet), and following 7 weeks of dietary restriction
(post-diet; n = 15), and outset pH and volatile fatty
acid concentrations (mean of 3 pre-diet days ± SD) in
the high (n = 5), medium (n = 5) and low (n = 5) weight-loss groups.

| | Pre-diet | Post-diet | P-value | High | Medium | Low | P-value |
|---|---|---|---|---|---|---|---|
| pH | 6.73 ± 0.24 | 6.72 ± 0.15 | 0.90 | 6.74 ± 0.04 | 6.77 ± 0.10 | 6.69 ± 0.43 | 0.90 |
| Acetate (mM) | 15.01 ± 5.84 | 11.68 ± 6.83 | <0.01 | 19.97 ± 5.45 | 14.52 ± 5.54 | 10.53 ± 1.67 | 0.02 |
| Propionate (mM) | 4.31 ± 1.10 | 2.96 ± 1.41 | <0.01 | 4.97 ± 1.06 | 4.31 ± 1.32 | 3.66 ± 0.54 | 0.17 |
| Butyrate (mM) | 1.47 ± 0.45 | 1.17 ± 0.72 | 0.02 | 1.73 ± 0.59 | 1.44 ± 0.38 | 1.23 ± 0.24 | 0.22 |
| BCVFA (mM) | 1.20 ± 0.47 | 0.91 ± 0.69 | 0.04 | 1.29 ± 0.71 | 1.30 ± 0.43 | 1.01 ± 0.15 | 0.58 |

TABLE 3

Associations between weight-loss and outset measures of
diversity. Univariate regression analysis was employed
to investigate associations with total proportion weight-
loss (corrected to week 0; logit transformation) as the
outcome variable and outset diversity measure (mean of
3 pre-diet days) as the explanatory variable.

| Explanatory variable | Coefficient | 95% CI | P value | R-squared |
|---|---|---|---|---|
| Inverse Simpson (logit transformation) | −0.002 | −0.004 to 0.0003 | 0.10 | 0.20 |
| Baseline | −2.25 | −2.40 to −2.10 | <0.01 | |
| Shannon-Weiner (squared transformation) | −0.02 | −0.03 to −0.004 | 0.02 | 0.35 |
| Baseline | −1.77 | −2.25 to −1.29 | <0.01 | |
| S.Obs | −0.0005 | −0.0009 to −0.0001 | 0.01 | 0.39 |
| Baseline | −1.50 | −2.15 to −0.85 | <0.01 | |

TABLE 4

Associations between weight-loss and outset VFA concentrations. Univariate
regression analysis was employed to investigate associations between total
proportion weight-loss (corrected to week 0; logit transformation).

| Outcome variable | Explanatory variable | Coefficient | 95% CI | P value | R-squared |
|---|---|---|---|---|---|
| Total proportion weight-loss | Outset acetate concentration | 0.03 | 0.01 to 0.04 | <0.01 | 0.52 |
| | Baseline | −2.79 | −3.05 to −2.53 | <0.01 | |
| | Outset butyrate concentration | 0.29 | 0.05 to 0.54 | 0.02 | 0.34 |
| | Baseline | −2.80 | −3.18 to −2.43 | <0.01 | |
| | Outset propionate concentration | 0.12 | 0.02 to 0.22 | 0.03 | 0.33 |
| | Baseline | −2.88 | −3.33 to −2.44 | <0.01 | |
| | Outset BCVFA concentration | 0.16 | −0.11 to 0.43 | 0.22 | 0.12 |
| | Baseline | −2.57 | −2.91 to −2.22 | <0.01 | |

TABLE 5

Relative abundance of outset bacterial genera (mean of 3 pre-diet days) between
animals grouped into quartiles by outset acetate concentrations (mean of
3 pre-diet days). Animals were split into quartiles depending on outset acetate
concentrations as follows: Quartile 1, n = 4, 9.45 mM ± 0.27 (mean ± SD);
Quartile 2, n = 4, 11.66 mM ± 1.04, Quartile 3, n = 3, 16.76 mM ± 1.13,
Quartile 4, n = 4, 22.63 mM ± 4.49. ANOVA analysis was employed to
evaluate group differences in the relative abundance of bacterial phyla,
and the resulting p-value was adjusted for multiple testing using the
Benjamini-Hochberg correction.

| | Quartiles of outset Acetate concentration | | | | | Benjamini-Hochberg |
| | 1 | 2 | 3 | 4 | SED | P-value |
|---|---|---|---|---|---|---|
| Unclassified | 0.690 | 0.661 | 0.549 | 0.596 | 0.039 | 0.376 |
| *Fibrobacter* | 0.080 | 0.110 | 0.287 | 0.201 | 0.077 | 0.133 |
| *Treponema* | 0.037 | 0.038 | 0.015 | 0.018 | 0.021 | 0.051 |
| *Phascolarctobacterium* | 0.027 | 0.023 | 0.014 | 0.010 | 0.021 | 0.133 |
| *Alkalitalea* | 0.027 | 0.019 | 0.035 | 0.002 | 0.082 | 0.620 |
| *Prevotella* | 0.016 | 0.012 | 0.020 | 0.016 | 0.039 | 0.992 |
| *Paraprevotella* | 0.012 | 0.012 | 0.008 | 0.021 | 0.021 | 0.404 |
| *Paludibacter* | 0.012 | 0.013 | 0.007 | 0.029 | 0.050 | 0.676 |
| *Alloprevotella* | 0.010 | 0.004 | 0.001 | 0.003 | 0.028 | 0.453 |
| *Ruminococcus* | 0.010 | 0.013 | 0.007 | 0.010 | 0.024 | 0.870 |
| *Oscillibacter* | 0.009 | 0.007 | 0.005 | 0.006 | 0.012 | 0.423 |
| *Barnesiella* | 0.008 | 0.009 | 0.003 | 0.032 | 0.055 | 0.542 |
| *Clostridium* XIVa | 0.007 | 0.007 | 0.006 | 0.004 | 0.013 | 0.423 |
| Lachnospiracea | 0.005 | 0.005 | 0.004 | 0.005 | 0.009 | 0.978 |
| *Rikenella* | 0.005 | 0.009 | 0.006 | 0.008 | 0.013 | 0.433 |
| *Phocaeicola* | 0.004 | 0.014 | 0.008 | 0.009 | 0.028 | 0.432 |
| *Anaeroplasma* | 0.004 | 0.007 | 0.004 | 0.003 | 0.015 | 0.423 |
| *Faecalitalea* | 0.003 | 0.003 | 0.001 | 0.002 | 0.010 | 0.115 |
| *Asteroleplasma* | 0.003 | 0.001 | 0.002 | 0.001 | 0.021 | 0.870 |
| *Macellibacteroides* | 0.003 | 0.000 | 0.000 | 0.000 | 0.023 | 0.579 |
| *Anaerovorax* | 0.003 | 0.002 | 0.001 | 0.001 | 0.004 | 0.027 |
| *Sphaerochaeta* | 0.002 | 0.002 | 0.000 | 0.000 | 0.006 | 0.021 |
| *Coprobacter* | 0.002 | 0.001 | 0.001 | 0.002 | 0.016 | 0.978 |
| *Pseudoflavonifractor* | 0.002 | 0.011 | 0.001 | 0.004 | 0.039 | 0.870 |
| *Sporobacter* | 0.002 | 0.002 | 0.001 | 0.002 | 0.005 | 0.316 |
| *Lachnobacterium* | 0.002 | 0.001 | 0.002 | 0.001 | 0.010 | 0.870 |
| *Intestinimonas* | 0.002 | 0.002 | 0.002 | 0.003 | 0.010 | 0.752 |
| *Clostridium* IV | 0.002 | 0.002 | 0.002 | 0.002 | 0.067 | 0.978 |
| *Faecalicoccus* | 0.001 | 0.001 | 0.000 | 0.000 | 0.007 | 0.133 |
| *Mobilitalea* | 0.001 | 0.001 | 0.000 | 0.000 | 0.005 | 0.051 |
| *Anaerorhabdus* | 0.001 | 0.001 | 0.001 | 0.000 | 0.010 | 0.376 |
| *Saccharibacteria* | 0.001 | 0.001 | 0.001 | 0.001 | 0.007 | 0.997 |
| *Anaerocella* | 0.001 | 0.001 | 0.001 | 0.000 | 0.007 | 0.455 |
| *Ethanoligenens* | 0.001 | 0.000 | 0.001 | 0.001 | 0.010 | 0.870 |
| *Roseburia* | 0.001 | 0.001 | 0.001 | 0.001 | 0.005 | 0.997 |
| *Mogibacterium* | 0.001 | 0.001 | 0.000 | 0.001 | 0.006 | 0.453 |
| *Saccharofermentans* | 0.001 | 0.001 | 0.001 | 0.000 | 0.007 | 0.752 |
| *Vampirovibrio* | 0.001 | 0.001 | 0.001 | 0.001 | 0.007 | 0.870 |
| *Candidatusendomicrobium* | 0.000 | 0.001 | 0.000 | 0.000 | 0.010 | 0.978 |
| *Streptococcus* | 0.000 | 0.000 | 0.001 | 0.001 | 0.010 | 0.316 |
| *Catabacter* | 0.000 | 0.000 | 0.000 | 0.000 | 0.005 | 0.978 |

Figure 12:
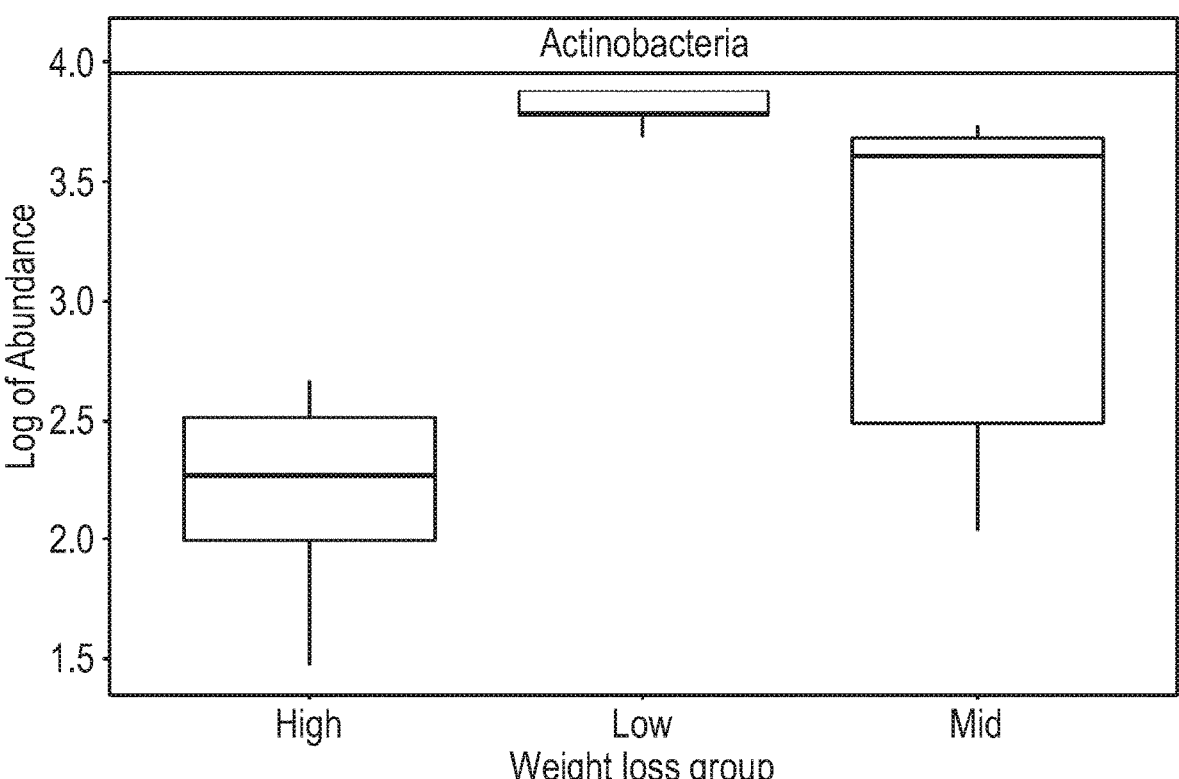
FIG. 12. The outset abundance of Actinobacteria between weight-loss groups following ANCOM analysis. n=15.

Example 2—Changes in Bacteria Abundance Following Weight-Loss and Associations with Weight-Loss Across all samples/time-points, Bacteriodetes were the most abundant phyla present, followed by the Firmicutes and Fibrobacteres. The relative abundance of Firmicutes and Tenericutes were significantly reduced following weight-loss (Table 6 and FIG. 1), and although the relative abundance of Bacteriodetes did not change significantly following weight-loss, the Firmicutes: Bacteriodetes ratio was increased following weight-loss (2.10±0.54 pre-diet to 2.54±0.56 post-diet; p=0.01). Similarly, the ratio of the fibre-digesting bacteria, Fibrobacteres:Firmicutes was increased following weight-loss (0.74±0.58 to 1.31±0.88; p=0.03). ANCOM and ANOVA analysis were employed to explore differences in the outset abundance (mean of 3 pre-diet days) of phyla between weight-loss groups. The outset abundance of Actinobacteria and Spirochaetes were found to be significantly greater in the low weight-loss group compared to the high weight-loss group (FIG. 12 and Table 7).

TABLE 6

Relative abundance of bacterial phyla before (pre-diet), and
after 7 weeks of dietary restriction (post-diet; n = 15).

| | Pre-diet | Post-diet | SED | Benjamini-Hochberg P-value |
|---|---|---|---|---|
| *Bacteroidetes* | 0.485 | 0.469 | 0.000 | 0.701 |
| *Firmicutes* | 0.239 | 0.187 | 0.000 | 0.011 |
| *Fibrobacteres* | 0.138 | 0.207 | 0.002 | 0.177 |
| Unclassified | 0.045 | 0.047 | 0.000 | 0.701 |

TABLE 6-continued

Relative abundance of bacterial phyla before (pre-diet), and
after 7 weeks of dietary restriction (post-diet; n = 15).

| | Pre-diet | Post-diet | SED | Benjamini-Hochberg P-value |
|---|---|---|---|---|
| *Spirochaetes* | 0.037 | 0.037 | 0.000 | 0.948 |
| *Proteobacteria* | 0.014 | 0.015 | 0.000 | 0.719 |
| *Tenericutes* | 0.006 | 0.003 | 0.000 | 0.011 |

TABLE 7

Relative abundance of outset bacterial phyla (mean of 3 pre-diet
days) between the three weight-loss groups (n = 5/group). ANOVA
analysis was employed to evaluate group differences in the relative
abundance of bacterial phyla, and the resulting p-value was adjusted
for multiple testing using the Benjamini-Hochberg correction.

| | Low | Mid | High | SED | Benjamini-Hochberg P-value |
|---|---|---|---|---|---|
| *Firmicutes* | 0.493 | 0.476 | 0.493 | 0.028 | 0.156 |
| *Bacteroidetes* | 0.082 | 0.180 | 0.219 | 0.037 | 0.949 |
| *Fibrobacteres* | 0.279 | 0.230 | 0.217 | 0.07 | 0.156 |
| *unclassified* | 0.058 | 0.049 | 0.034 | 0.024 | 0.156 |
| *Spirochaetes* | 0.053 | 0.042 | 0.022 | 0.021 | 0.033 |
| *Proteobacteria* | 0.020 | 0.016 | 0.009 | 0.016 | 0.132 |
| *Tenericutes* | 0.009 | 0.005 | 0.005 | 0.014 | 0.156 |
| *Verrucomicrobia* | 0.001 | 0.001 | 0.001 | 0.007 | 0.909 |
| *Candidatus Saccharibacteria* | 0.003 | 0.002 | 0.001 | 0.005 | 0.890 |
| *Actinobacteria* | 0.001 | 0.000 | 0.001 | 0.006 | 0.011 |
| *Elusimicrobia* | 0.000 | 0.000 | 0.000 | 0.008 | 0.909 |

Figure 13:
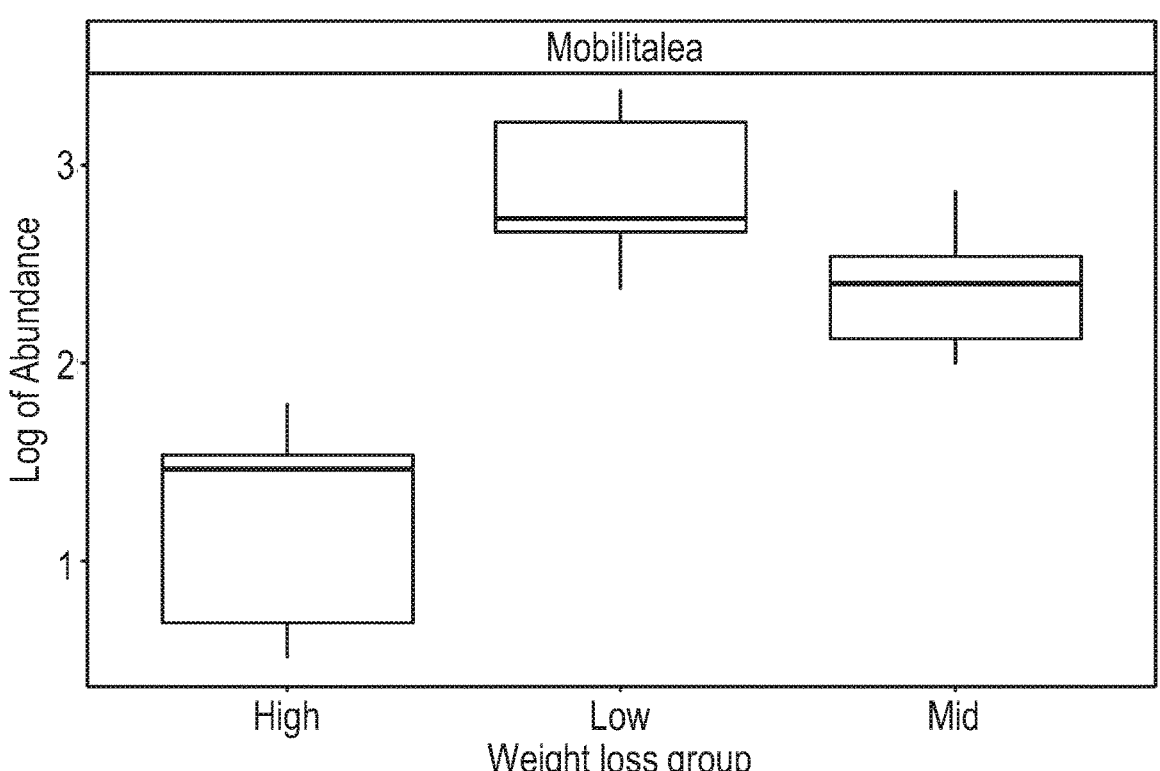
FIG. 13. The outset abundance of *Mobilitalea* between weight-loss groups following ANCOM analysis. n=15.

At the genera level, whilst the largest proportions of samples were unclassified at this level, *Fibrobacter* was the second-most abundant genus across all samples/time-points. A number of genera were altered in abundance following weight-loss: *Rikenella* and *Anaerorhabdus* (both belonging to the Bacteroidetes phyla) were increased in relative abundance (Table 8 and FIG. 2), whilst *Prevotella, Alloprevotella* (belonging to the Bacteroidetes phyla), *Clostridium* XIVa, *Phascolarctobacterium*, and *Pseudoflavonifractor* (belonging to the Firmicutes phyla) and *Anaeroplasma* (belonging to the Tenericutes phyla) were reduced in abundance (Table 8 and FIG. 1B). The outset abundance of *Mobilitalea* genus (belonging to the Firmicutes phyla) was found to be significantly greater in low compared to high weight-loss groups following ANCOM and ANOVA analysis (FIG. 13 and Table 9).

TABLE 8

Relative abundance of bacterial genera before (pre-diet), and
after 7 weeks of dietary restriction (post-diet; n = 15).

| | Pre-diet | Post-diet | SED | Benjamini-Hochberg P-value |
|---|---|---|---|---|
| *Phascolarctobacterium* | 0.019 | 0.009 | 0.009 | 0.005 |
| *Prevotella* | 0.016 | 0.007 | 0.008 | 0.005 |
| *Anaeroplasma* | 0.004 | 0.002 | 0.004 | 0.005 |
| *Coprobacter* | 0.002 | 0.001 | 0.005 | 0.005 |
| *Roseburia* | 0.001 | 0.000 | 0.002 | 0.005 |
| *Anaerorhabdus* | 0.001 | 0.006 | 0.008 | 0.005 |
| *Candidalusendomicrobium* | 0.000 | 0.001 | 0.003 | 0.005 |
| *Catabacter* | 0.000 | 0.001 | 0.003 | 0.005 |
| *Clostridium* XIVa | 0.006 | 0.004 | 0.004 | 0.009 |
| *Alloprevotella* | 0.005 | 0.001 | 0.007 | 0.012 |
| *Streptococcus* | 0.001 | 0.002 | 0.005 | 0.022 |
| *Rikenella* | 0.007 | 0.011 | 0.006 | 0.024 |
| *Pseudoflavonifractor* | 0.005 | 0.000 | 0.012 | 0.035 |

TABLE 8-continued

Relative abundance of bacterial genera before (pre-diet), and
after 7 weeks of dietary restriction (post-diet; n = 15).

| | Pre-diet | Post-diet | SED | Benjamini-Hochberg P-value |
|---|---|---|---|---|
| *Saccharofermentans* | 0.001 | 0.001 | 0.003 | 0.035 |
| *Faecalitalea* | 0.002 | 0.001 | 0.006 | 0.066 |
| *Anaerovorax* | 0.002 | 0.001 | 0.003 | 0.090 |
| Lachnospiracea | 0.005 | 0.004 | 0.005 | 0.099 |
| *Paraprevotella* | 0.013 | 0.010 | 0.008 | 0.103 |
| *Faecalicoccus* | 0.001 | 0.000 | 0.003 | 0.111 |
| *Anaerocella* | 0.001 | 0.001 | 0.003 | 0.111 |
| *Macellibacteroides* | 0.001 | 0.000 | 0.005 | 0.125 |
| *Lachnobacterium* | 0.002 | 0.001 | 0.003 | 0.134 |
| *Fibrobacter* | 0.161 | 0.228 | 0.042 | 0.150 |
| *Ruminococcus* | 0.010 | 0.008 | 0.009 | 0.172 |
| *Asteroleplasma* | 0.002 | 0.001 | 0.006 | 0.172 |
| Saccharibacteria | 0.001 | 0.001 | 0.002 | 0.172 |
| *Mogibacterium* | 0.001 | 0.001 | 0.001 | 0.175 |
| *Phocaeicola* | 0.009 | 0.006 | 0.009 | 0.185 |
| *Sphaerochaeta* | 0.001 | 0.002 | 0.003 | 0.185 |
| *Rreponema* | 0.028 | 0.031 | 0.008 | 0.216 |
| *Alkalitalea* | 0.020 | 0.016 | 0.028 | 0.287 |
| Unclassified | 0.629 | 0.597 | 0.017 | 0.300 |
| *Sporobacter* | 0.002 | 0.002 | 0.002 | 0.354 |
| *Mobilitalea* | 0.001 | 0.001 | 0.003 | 0.740 |
| *Paludibacter* | 0.016 | 0.019 | 0.019 | 0.994 |
| *Barnesiella* | 0.014 | 0.011 | 0.018 | 0.994 |
| *Sscillibacter* | 0.007 | 0.007 | 0.004 | 0.994 |
| *Intestinimonas* | 0.002 | 0.002 | 0.005 | 0.994 |
| *Clostridium* IV | 0.002 | 0.002 | 0.004 | 0.994 |
| *Ethanoligenens* | 0.001 | 0.001 | 0.006 | 0.994 |
| *Vampirovibrio* | 0.001 | 0.001 | 0.003 | 0.994 |

TABLE 9

Relative abundance of outset bacterial genera (mean of 3 pre-diet
days) between the three weight-loss groups (n = 5/group). ANOVA
analysis was employed to evaluate group differences in the relative
abundance of bacterial phyla, and the resulting p-value was adjusted
for multiple testing using the Benjamini-Hochberg correction.

| | Low | Mid | High | SED | Benjamini-Hochber P-value |
|---|---|---|---|---|---|
| Unclassified | 0.691 | 0.616 | 0.581 | 0.032 | 0.434 |
| *Fibrobacter* | 0.083 | 0.181 | 0.221 | 0.070 | 0.328 |
| *Treponema* | 0.034 | 0.034 | 0.016 | 0.020 | 0.205 |
| *Phascolarctobacterium* | 0.026 | 0.018 | 0.013 | 0.019 | 0.424 |
| *Alkalitalea* | 0.023 | 0.016 | 0.021 | 0.069 | 0.880 |
| *Prevotella* | 0.015 | 0.013 | 0.020 | 0.029 | 0.872 |
| *Paraprevotella* | 0.013 | 0.015 | 0.012 | 0.020 | 0.880 |
| *Barnesiella* | 0.011 | 0.004 | 0.026 | 0.043 | 0.690 |
| *Ruminococcus* | 0.011 | 0.012 | 0.009 | 0.018 | 0.872 |
| *Paludibacter* | 0.010 | 0.015 | 0.022 | 0.041 | 0.872 |
| *Alloprevotella* | 0.009 | 0.004 | 0.002 | 0.023 | 0.706 |
| *Clostridium* XIVa | 0.008 | 0.005 | 0.005 | 0.010 | 0.476 |
| *Oscillibacter* | 0.008 | 0.007 | 0.006 | 0.010 | 0.872 |
| *Phocaeicola* | 0.006 | 0.011 | 0.009 | 0.026 | 0.872 |
| *Anaeroplasma* | 0.006 | 0.003 | 0.003 | 0.012 | 0.559 |
| *Rikenella* | 0.006 | 0.009 | 0.006 | 0.010 | 0.434 |
| Lachnospiracea | 0.006 | 0.005 | 0.004 | 0.007 | 0.770 |
| *Faecalitalea* | 0.003 | 0.002 | 0.001 | 0.010 | 0.434 |
| *Asteroleplasma* | 0.003 | 0.001 | 0.001 | 0.016 | 0.872 |
| *Anaerovorax* | 0.002 | 0.002 | 0.001 | 0.005 | 0.144 |
| *Coprobacter* | 0.002 | 0.002 | 0.001 | 0.012 | 0.750 |
| *Sporobacter* | 0.002 | 0.002 | 0.001 | 0.004 | 0.328 |
| *Sphaerochaeta* | 0.002 | 0.001 | 0.000 | 0.007 | 0.150 |
| *Macellibacteroides* | 0.002 | 0.001 | 0.000 | 0.019 | 0.872 |
| *Pseudoflavonifractor* | 0.002 | 0.009 | 0.004 | 0.030 | 0.872 |
| *Lachnobacterium* | 0.002 | 0.001 | 0.001 | 0.008 | 0.872 |
| *Intestinimonas* | 0.002 | 0.002 | 0.003 | 0.007 | 0.640 |
| *Clostridium* IV | 0.002 | 0.002 | 0.002 | 0.005 | 0.706 |
| *Faecalicoccus* | 0.001 | 0.001 | 0.000 | 0.006 | 0.328 |
| *Mobilitalea* | 0.001 | 0.001 | 0.000 | 0.004 | 0.041 |

TABLE 9-continued

Relative abundance of outset bacterial genera (mean of 3 pre-diet days) between the three weight-loss groups (n = 5/group). ANOVA analysis was employed to evaluate group differences in the relative abundance of bacterial phyla, and the resulting p-value was adjusted for multiple testing using the Benjamini-Hochberg correction.

| | Low | Mid | High | SED | Benjamini-Hochber P-value |
|---|---|---|---|---|---|
| Anaerorhabdus | 0.001 | 0.000 | 0.001 | 0.009 | 0.746 |
| Roseburia | 0.001 | 0.001 | 0.001 | 0.004 | 0.872 |
| Saccharofermentans | 0.001 | 0.000 | 0.001 | 0.005 | 0.690 |
| Vampirovibrio | 0.001 | 0.001 | 0.001 | 0.005 | 0.872 |
| Saccharibacteria | 0.001 | 0.001 | 0.001 | 0.005 | 0.872 |
| Ethanoligeneris | 0.001 | 0.001 | 0.001 | 0.008 | 0.872 |
| Anaerocella | 0.001 | 0.001 | 0.000 | 0.006 | 0.872 |
| Mogibacterium | 0.001 | 0.001 | 0.001 | 0.005 | 0.872 |
| Candidatusendomicrobium | 0.000 | 0.000 | 0.001 | 0.007 | 0.915 |
| Catabacter | 0.000 | 0.000 | 0.000 | 0.004 | 0.872 |
| Streptococcus | 0.000 | 0.000 | 0.001 | 0.007 | 0.287 |

A total of 61 OTUs belonging to 13 genera were found to be significantly different in abundance following weight-loss: 7 of which were decreased in abundance following weight-loss and the remaining 51 were increased in abundance. Significant differences in outset OTU abundance were also identified between the weight-loss groups: the greatest number of differences were identified between the high and low weight-loss groups (159 OTUs belonging to 18 genera significantly different, 101 of which were greater in the high compared to low weight-loss group). A total of 48 OTUs belonging to 9 genera were found to be significantly different in outset abundance between the low and mid weight-loss groups, whilst 28 OTUs belonging to 6 genera were found to be significantly different between the mid and high weight-loss groups.

Example 3—Microbiome Structure as a Predictor of Weight Loss

Figure 2:
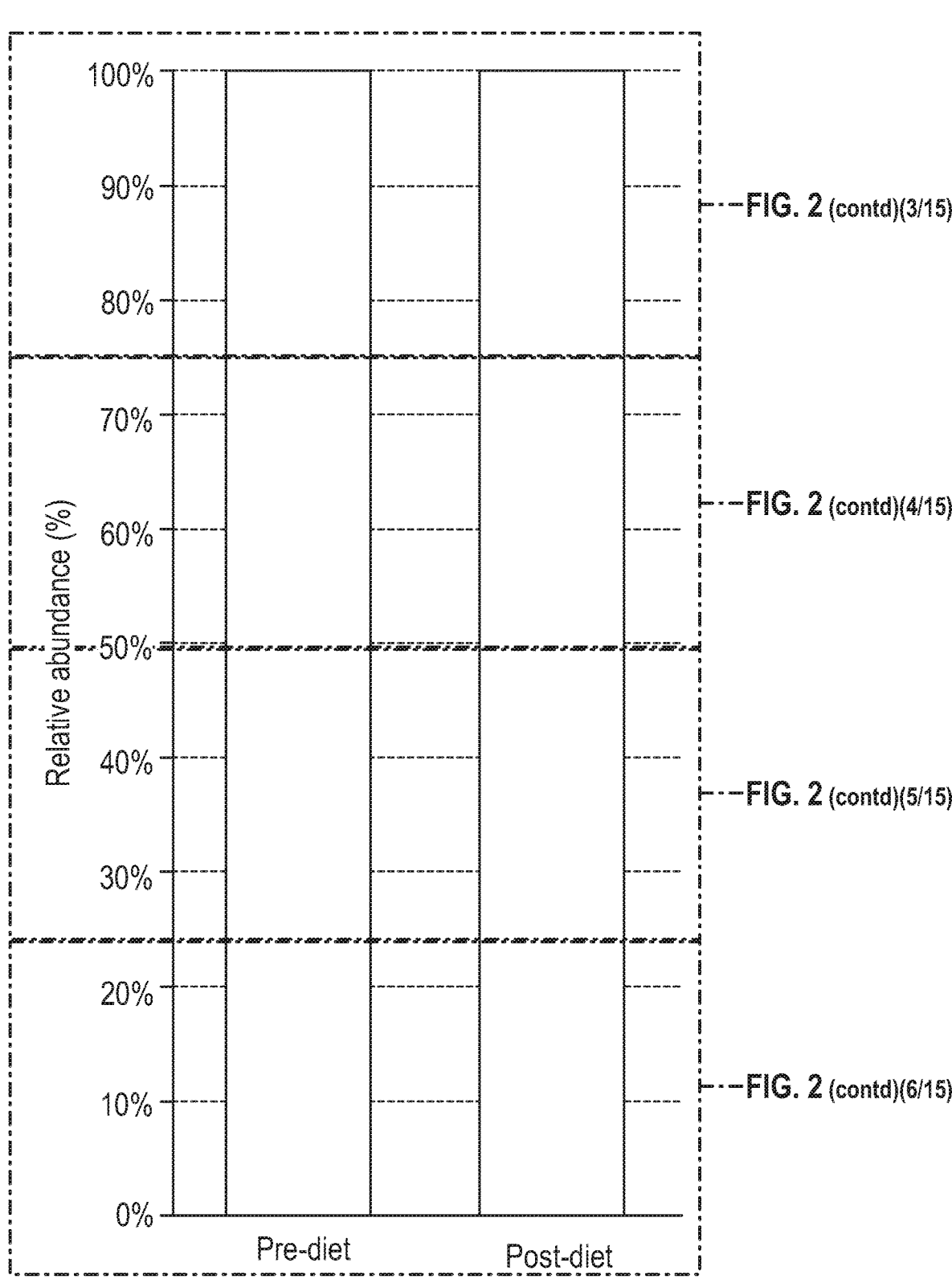
FIG. 2. Stacked histogram illustrating the relative abundance of the dominant bacterial genera (present at >0.05%) before (pre-diet), and after 7 weeks of dietary restriction (post-diet; n=15).
Figure 2:
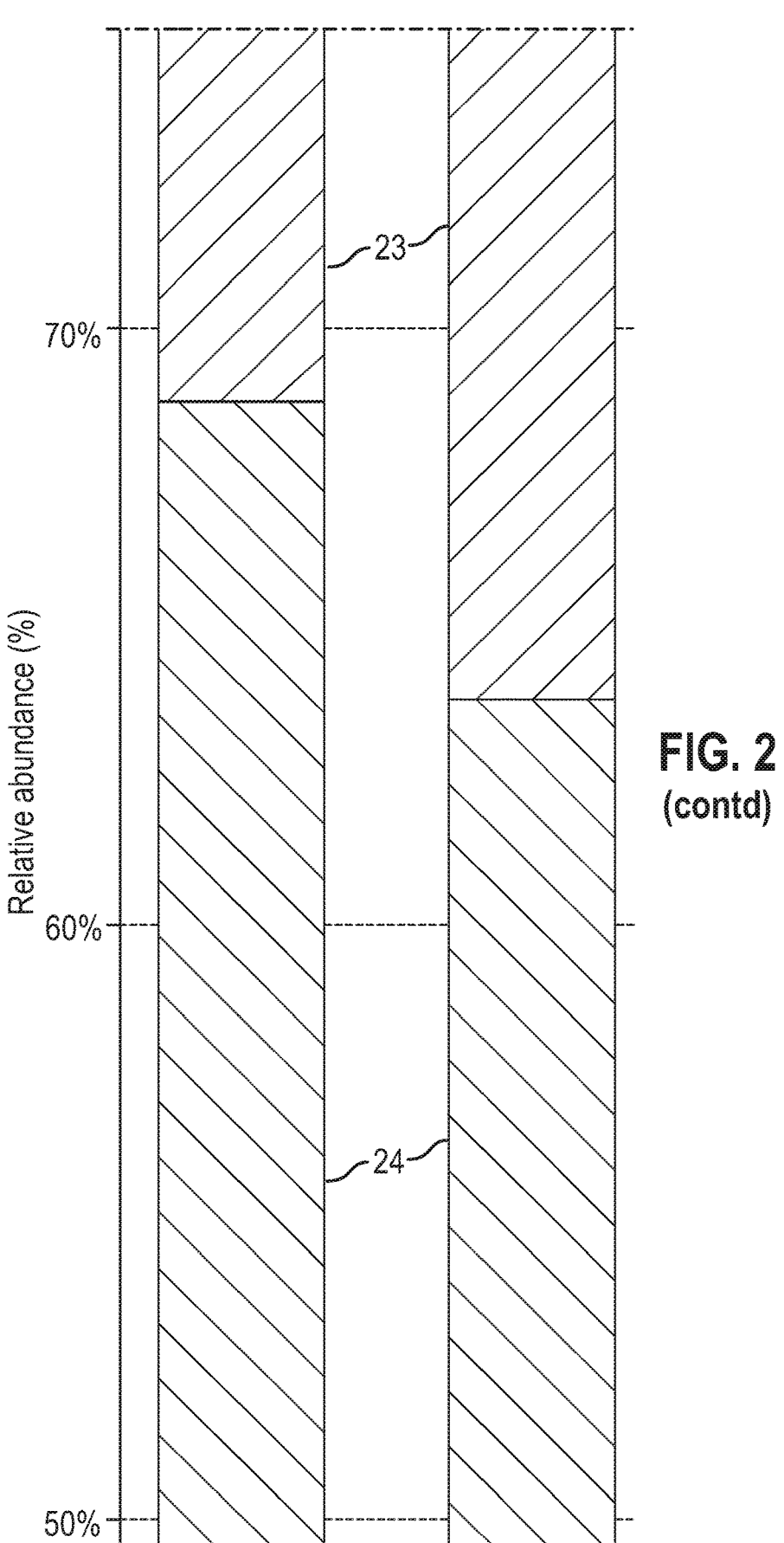
Figure 2:
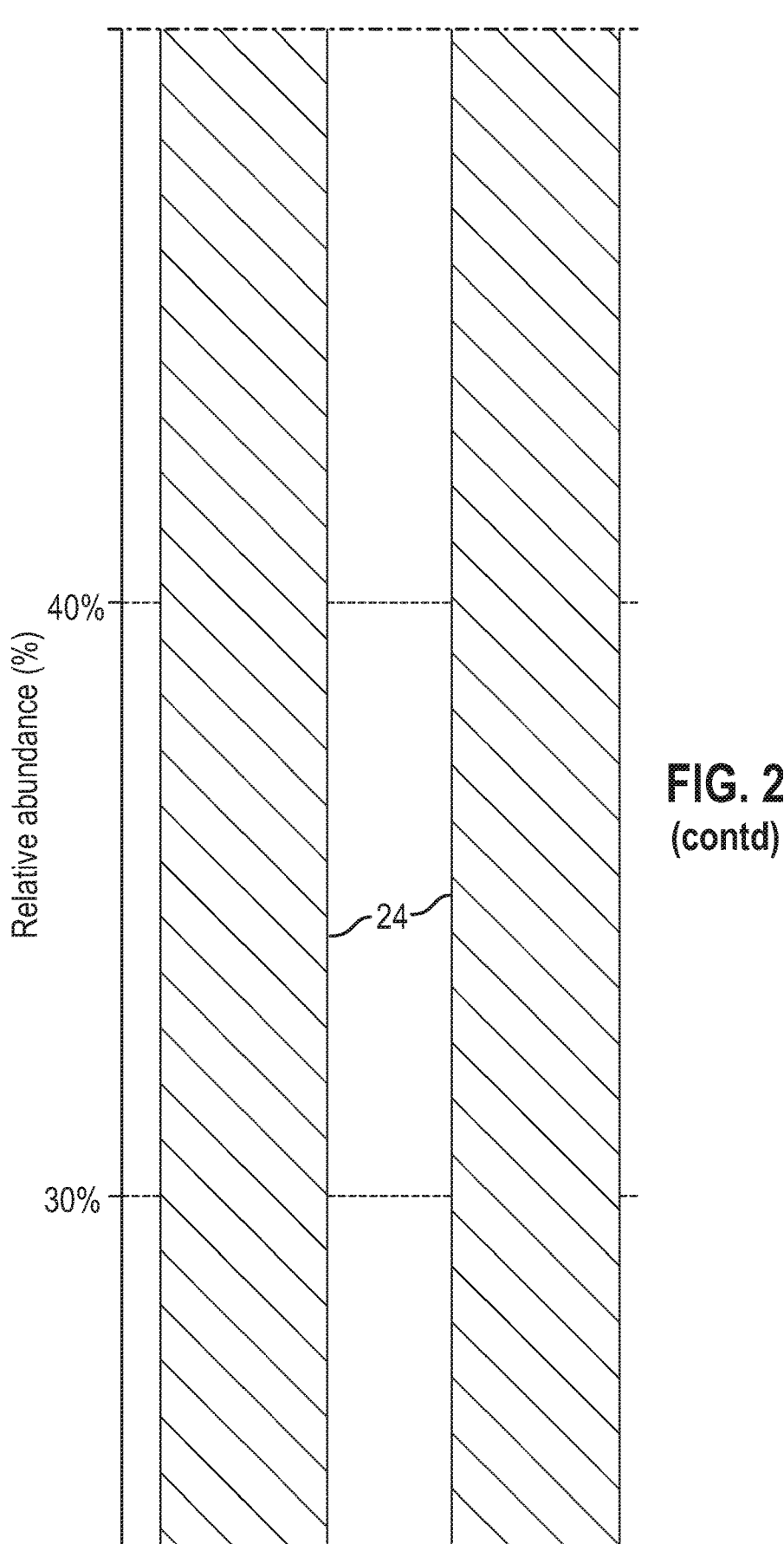
Figure 2:
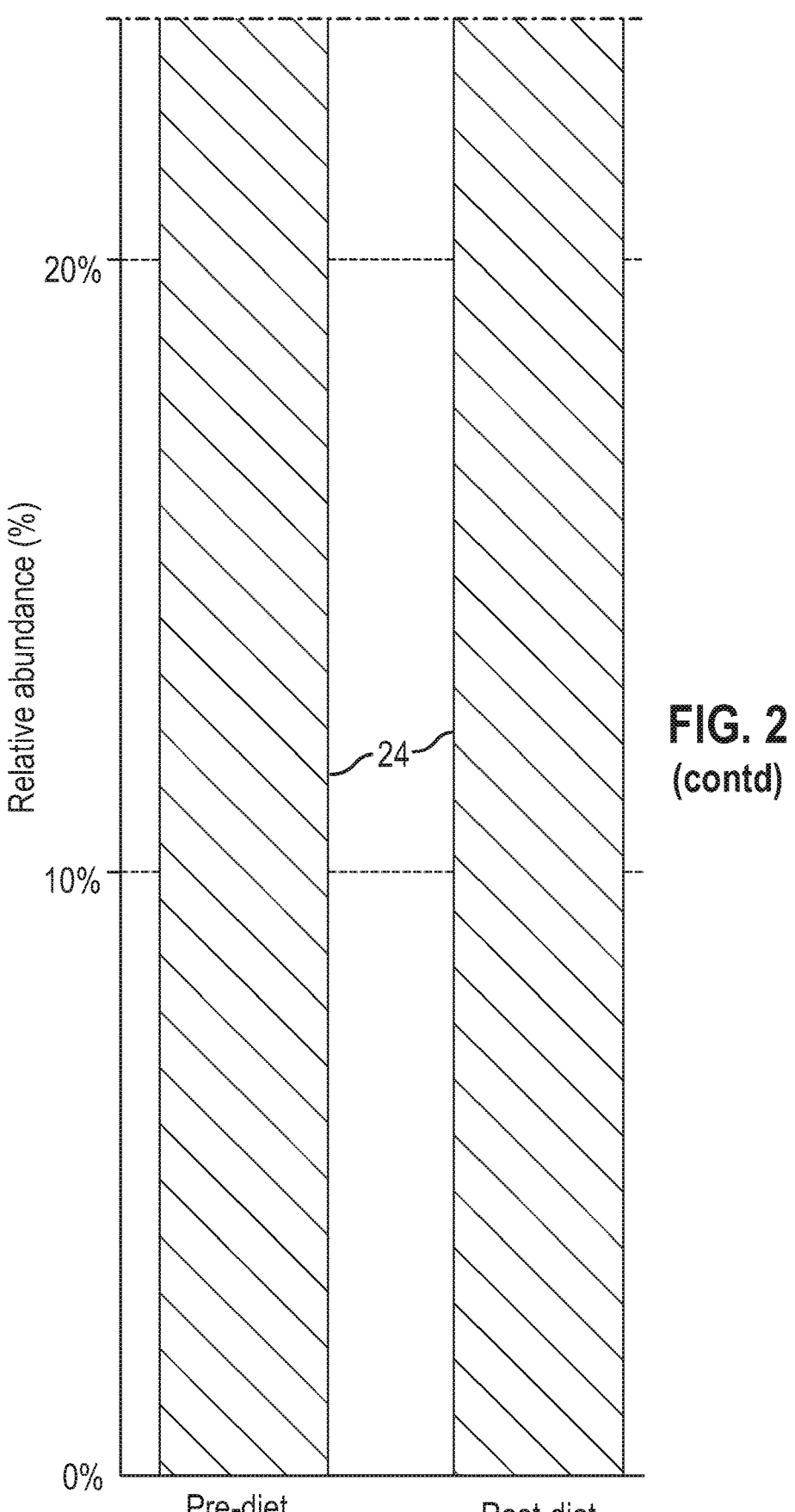
Figure 3:
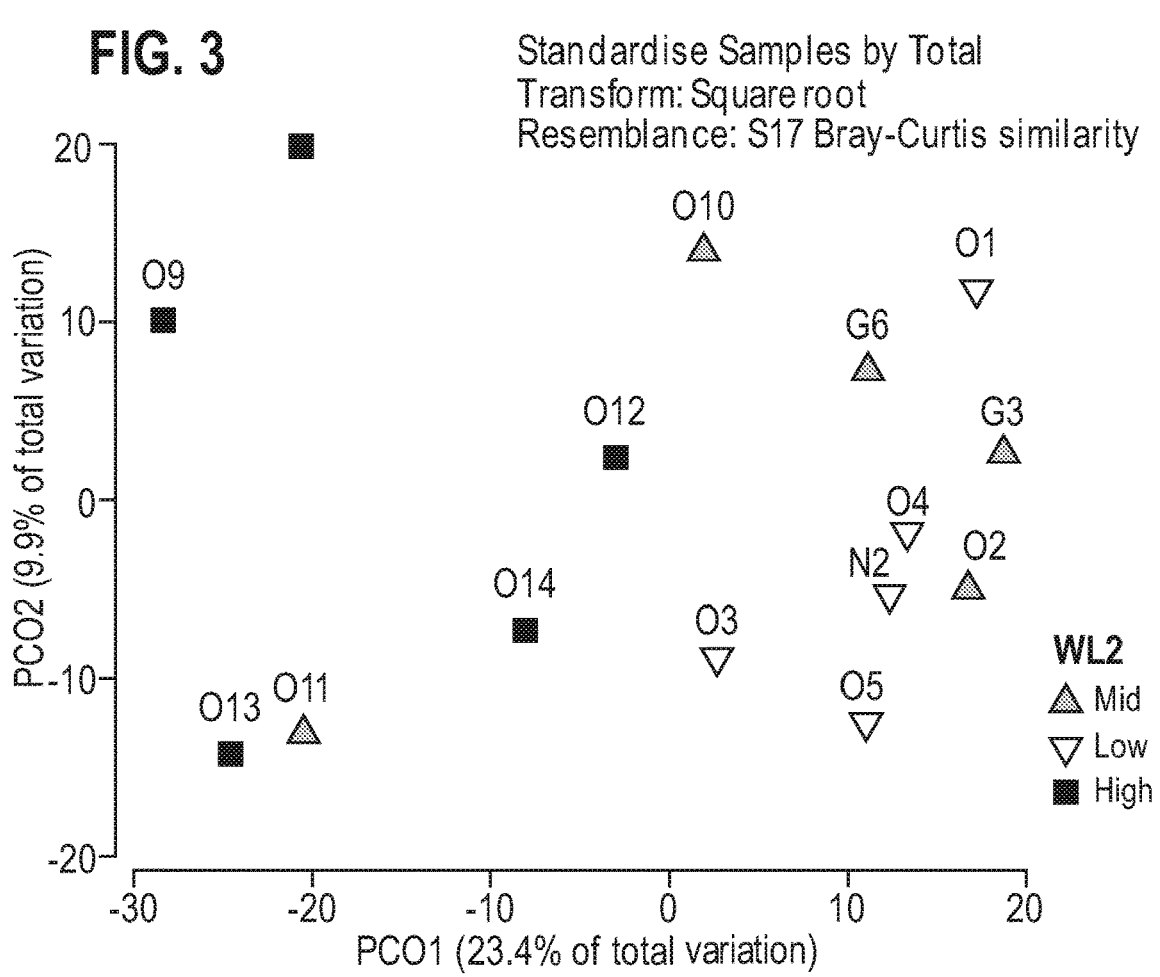
FIG. 3. Distance-based redundancy analysis illustrating the outset bacterial community structure attributable to weight-loss group (n=15).
Figure 4:
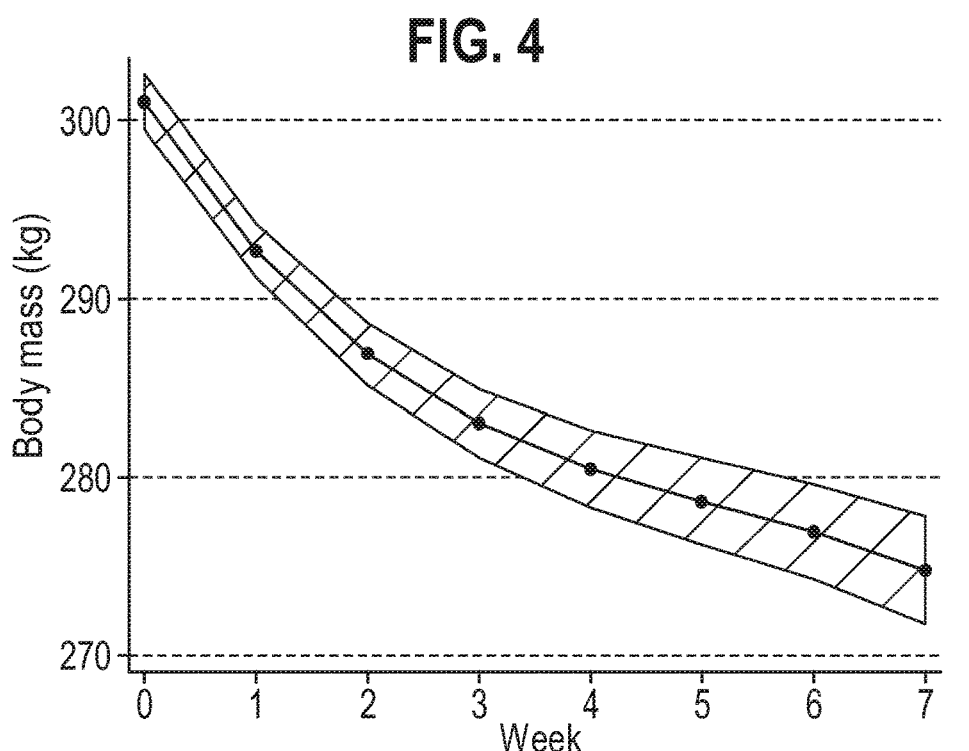
FIG. 4. Marginal mean plot derived demonstrating predicted body mass change over the 7 week dietary restriction phase of the study (n=15). Shaded area=95% confidence intervals.
Figure 5:
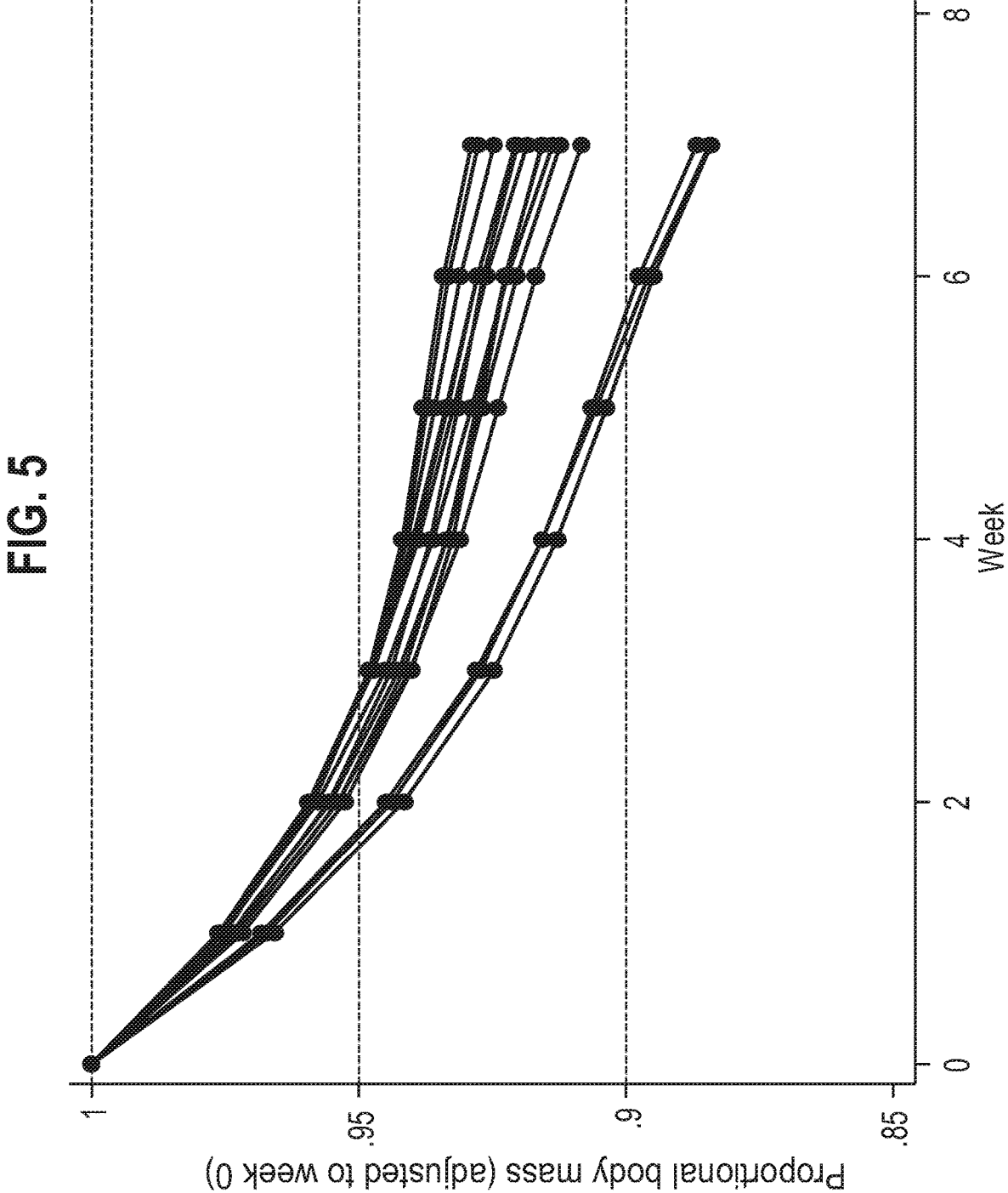
FIG. 5. Predicted cumulative proportional weight-loss for individual animals over the 7 week dietary-restriction phase of the study (adjusted to Week 0; n=15).
Figure 14:
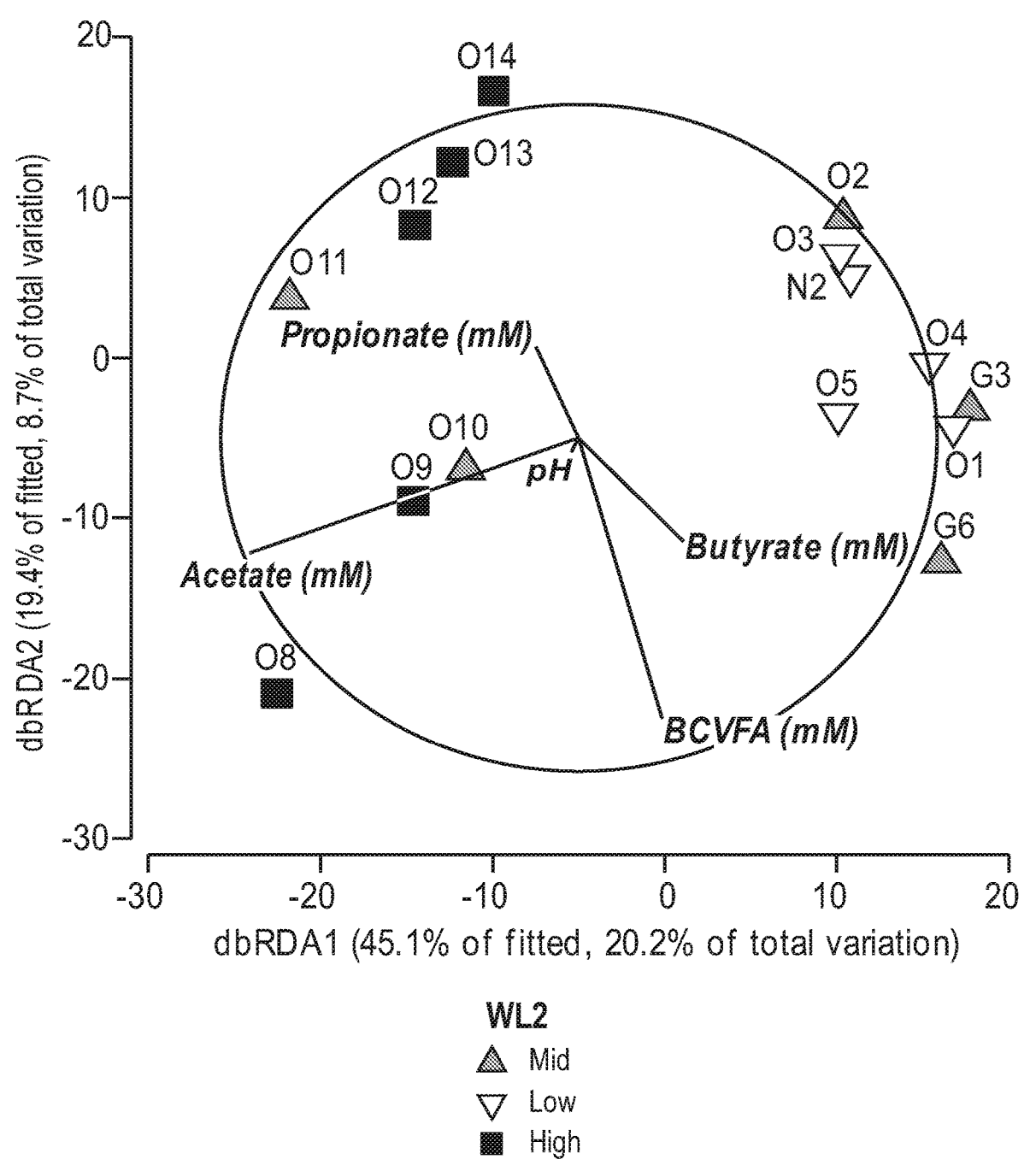
FIG. 14. Distance-based redundancy analysis illustrating associations between outset bacterial community structure in individual animals in the low, mid, and high weight-loss groups and outset faecal VFA concentrations. n=15.

In an attempt to ascertain whether the outset bacterial community structure could predict subsequent weight-loss, PERMANOVA and ANOSIM analysis was employed. There were significant differences in outset bacterial community structure at the OTU level, whereby the greatest divergence was found between the high and low weight-loss groups (R=0.67, p<0.01; Table 10). Distance-based redundancy analysis (dbRDA) was employed to summarise the variation in outset bacterial community structure attributable to weight-loss group (FIG. 2). Whilst there was some overlapping between the groups, animals in the low weight-loss group clustered together and markedly separately from those in the high weight-loss group where there was more variation in outset bacterial structure between animals. A second dbRDA analysis was performed to evaluate the contribution of outset VFA concentrations and pH to outset bacterial community structure (FIG. 14). As illustrated by FIG. 14, outset acetate concentration correlated strongly with differences in outset bacterial community structure between the weight-loss groups.

TABLE 10

Effect of weight loss group on the structure of bacterial communities in equine faeces. Significant P-values for PERMANOVA (P < 0.05) are highlighted. Anosim R values indicate the degree of separation between samples (0 = very similar; 1 = highly dissimilar), with significant R-values (with P < 0.05) shown in bold.

| | Group | Low | Medium |
|---|---|---|---|
| PERMANOVA (p-value) | Medium | 0.41 | |
| | High | 0.008 | 0.06 |
| ANOSIM (R-value) | Medium | 0.028 | |
| | High | 0.668 | 0.316 |

REFERENCES

1. Bouter, K. E., van Raalte, D. H., Groen, A. K. & Nieuwdorp, M. Role of the Gut Microbiome in the Pathogenesis of Obesity and Obesity-Related Metabolic Dysfunction. *Gastroenterology* 152, 1671-1678 (2017).
2. Mathur, R. & Barlow, G. M. Obesity and the microbiome. *Expert Rev. Gastroenterol. Hepatol.* 9, 1087-1099 (2015).
3. Turnbaugh, P. J. et al. A core gut microbiome in obese and lean twins. *Nature* 457, 480-484 (2009).
4. Turnbaugh, P. J. et al. An obesity-associated gut microbiome with increased capacity for energy harvest. *Nature* 444, 1027-1031 (2006).
5. Duncan, S. H. et al. Human colonic microbiota associated with diet, obesity and weight loss. *Int. J. Obes.* 2005 32, 1720-1724 (2008).
6. Ley, R. E., Turnbaugh, P. J., Klein, S. & Gordon, J. I. Microbial ecology: human gut microbes associated with obesity. *Nature* 444, 1022-1023 (2006).
7. Handl, S. et al. Faecal microbiota in lean and obese dogs. *FEMS Microbiol. Ecol.* 84, 332-343 (2013).
8. Morrison, P. K. et al. The Equine Gastrointestinal Microbiome: Impacts of Age and Obesity. *Front. Microbiol.* 9, (2018).
9. Geor, R. J., Coenen, M. & Harris, P. *Equine Applied and Clinical Nutrition: Health, Welfare and Performance.* (Elsevier Health Sciences, 2013).
10. Jensen, R. B., Danielsen, S. H. & Tauson, A.-H. Body condition score, morphometric measurements and estimation of body weight in mature Icelandic horses in Denmark. *Acta Vet. Scand.* 58, 59 (2016).
11. Potter, S. J., Bamford, N. J., Harris, P. A. & Bailey, S. R. Prevalence of obesity and owners' perceptions of body condition in pleasure horses and ponies in south-eastern Australia. *Aust. Vet. J.* 94, 427-432 (2016).
12. Robin, C. A. et al. Prevalence of and risk factors for equine obesity in Great Britain based on owner-reported body condition scores. *Equine Vet. J.* 47, 196-201 (2015).
13. Argo, C. M. et al. Weight loss resistance: a further consideration for the nutritional management of obese Equidae. *Vet. J. Lond. Engl.* 1997 194, 179-188 (2012).
14. Dougal, K. et al. Characterisation of the Faecal Bacterial Community in Adult and Elderly Horses Fed a High Fibre, High Oil or High Starch Diet Using 454 Pyrosequencing. *PLOS ONE* 9, e87424 (2014).
15. Fernandes, K. A. et al. Faecal Microbiota of Forage-Fed Horses in New Zealand and the Population Dynamics of Microbial Communities following Dietary Change. *PLOS ONE* 9, e112846 (2014).

16. Harlow, B. E., Donley, T. M., Lawrence, L. M. & Flythe, M. D. Effect of starch source (corn, oats or wheat) and concentration on fermentation by equine faecal microbiota in vitro. *J. Appl. Microbiol.* 119, 1234-1244 (2015).

17. Steelman, S. M., Chowdhary, B. P., Dowd, S., Suchodolski, J. & Janečka, J. E. Pyrosequencing of 16S rRNA genes in fecal samples reveals high diversity of hindgut microflora in horses and potential links to chronic laminitis. *BMC Vet. Res.* 8, 231 (2012).

18. Elzinga, S. E. Comparison of the Fecal Microbiota in Horses With Equine Metabolic Syndrome and Metabolically Normal Controls Fed a Similar All-Forage Diet. *J. Equine Vet. Sci.* v. 44, 9-16 (2016).

19. Dougal, K. et al. Changes in the Total Fecal Bacterial Population in Individual Horses Maintained on a Restricted Diet Over 6 Weeks. *Front. Microbiol.* 8, (2017).

20. Dugdale, A. H. A., Grove-White, D., Curtis, G. C., Harris, P. A. & Argo, C. M. Body condition scoring as a predictor of body fat in horses and ponies. *Vet. J. Lond. Engl.* 1997 194, 173-178 (2012).

21. Hart, M. L., Meyer, A., Johnson, P. J. & Ericsson, A. C. Comparative Evaluation of DNA Extraction Methods from Feces of Multiple Host Species for Downstream Next-Generation Sequencing. *PLOS ONE* 10, e0143334 (2015).

22. *Remington: the science and practice of pharmacy*. (Lippincott Williams & Wilkins, 2000).

23. Ream, W. & Field, K. G. *Molecular Biology Techniques: An Intensive Laboratory Course*. (Academic Press, 1998).

24. Methods in Enzymology by Colowick, S. P. & Kaplan, N. O (Eds.): Academic Press.

25. Weir, D. M., Herzenberg, L. A., Blackwell, C. & Herzenberg, L. A. *Handbook of experimental immunology*. (Blackwell Scientific Publications, 1986).

26. Sambrook, J., Russell, D. W. & Laboratory, C. S. H. *Molecular cloning: a laboratory manual*. (Cold Spring Harbor, N.Y.: Cold Spring Harbor Laboratory, 2001).

27. Birdi, K. S. *Handbook of Surface and Colloid Chemistry*. (Taylor & Francis, 1997).

28. PCR (*Introduction to Biotechniques Series*), 2nd ed. (Newton & Graham eds., 1997, Springer Verlag).

29. *Short Protocols in Molecular Biology*. (Current Protocols, 2002).

30. *Current Protocols in Molecular Biology* (F. M. Ausubel et al., eds., 1987) Supplement 30.

31. Smith, T. F. & Waterman, M. S. Comparison of biosequences. *Adv. Appl. Math.* 2, 482-489 (1981).

32. Dugdale, A. H. A., Curtis, G. C., Milne, E., Harris, P. A. & Argo, C. M. Assessment of body fat in the pony: part II. Validation of the deuterium oxide dilution technique for the measurement of body fat. *Equine Vet. J.* 43, 562-570 (2011).

33. Yu, Z. & Morrison, M. Improved extraction of PCR-quality community DNA from digesta and fecal samples. *BioTechniques* 36, 808-812 (2004).

34. Belanche, A., de la Fuente, G., Pinloche, E., Newbold, C. J. & Balcells, J. Effect of diet and absence of protozoa on the rumen microbial community and on the representativeness of bacterial fractions used in the determination of microbial protein synthesis. *J. Anim. Sci.* 90, 3924-3936 (2012).

35. Belanche, A., Jones, E., Parveen, I. & Newbold, C. J. A Metagenomics Approach to Evaluate the Impact of Dietary Supplementation with Ascophyllum nodosum or *Laminaria digitata* on Rumen Function in Rusitec Fermenters. *Front. Microbiol.* 7, (2016).

36. Fuente, G. de la et al. Pros and Cons of Ion-Torrent Next Generation Sequencing versus Terminal Restriction Fragment Length Polymorphism T-RFLP for Studying the Rumen Bacterial Community. *PLOS ONE* 9, e101435 (2014).

37. Wang, Q., Garrity, G. M., Tiedje, J. M. & Cole, J. R. Naïve Bayesian Classifier for Rapid Assignment of rRNA Sequences into the New Bacterial Taxonomy. *Appl. Environ. Microbiol.* 73, 5261-5267 (2007).

38. STEWART, C. S. & DUNCAN, S. H. The Effect of Avoparcin on Cellulolytic Bacteria of the Ovine Rumen. *Microbiology* 131, 427-435 (1985).

39. Gihring, T. M., Green, S. J. & Schadt, C. W. Massively parallel rRNA gene sequencing exacerbates the potential for biased community diversity comparisons due to variable library sizes. *Environ. Microbiol.* 14, 285-290 (2012).

40. Benjamini, Y. & Hochberg, Y. Controlling the false discovery rate: a practical and powerful approach to multiple testing. *J. R. Stat. Soc.* Ser. B Methodol. 57, 289-300 (1995).

41. Love, M. I., Huber, W. & Anders, S. Moderated estimation of fold change and dispersion for RNA-seq data with DESeq2. *Genome Biol.* 15, 550 (2014).

42. Legendre, P. & Anderson, M. J. Distance-based redundancy analysis: testing multispecies responses in multifactorial ecological experiments. *Ecol. Monogr.* 69, 1-24 (1999).

The invention claimed is:

1. A method of reducing body mass in an animal of the genus *Equus* in need thereof, the method comprising:

a) quantifying a plurality of bacterial taxa in a fecal sample obtained from the animal and calculating a diversity measure of the bacterial taxa present in the fecal sample, wherein the step of calculating the diversity measure comprises calculating an Inverse Simpson diversity value according to formula (I):

(I) $1/\Sigma Pi2$, wherein Pi is the proportion of individuals belonging to species i;

b) identifying the animal as having a Body Condition Scoring (BCS) value of at least 6, wherein the fecal sample obtained from the animal comprises a calculated Inverse Simpson diversity value from about 10 to about 70; and c) restricting caloric intake through a calorie-restricted diet plan, wherein the calorie-restricted diet plan has a duration of from about 7 weeks to about 16 weeks, and wherein the calorie-restricted diet plan comprises dry matter in an amount from about 1% to about 1.50% relative to the animal's body mass per day during the period of caloric restriction, and wherein the calorie-restricted diet plan reduces body mass ranging from about 1.14% to about 1.25% per week.

2. The method of claim 1, wherein a calculated Inverse Simpson diversity of less than 75, 70, 65, 60, 55, 50, 45, 40, 35 or 30 is predictive of loss of at least 8% outset body mass after the period of caloric restriction.

3. The method of claim 1, wherein the step of calculating the diversity measure comprises calculating a Shannon-Weiner diversity value according to formula (II):

(II) $-\Sigma 22$ Pi ln (Pi), wherein Pi is the proportion of individuals belonging to species i, wherein a fecal sample comprising a calculated Shannon-Weiner diversity value from about 4 to about 6 indicates the diversity measure is predictive of loss of at least 8% outset body mass after the period of caloric restriction.

4. The method of claim 1, wherein the step of calculating the diversity measure comprises calculating the number of different bacterial species present in the sample.

5. The method of claim 4, wherein a fecal sample comprising between about 1000and about 1900 different bacterial species is predictive of loss of at least 8% outset body mass after the period of caloric restriction.

6. A method of reducing body mass in an animal of the genus Equus in need thereof, the method comprising:

a) quantifying an abundance and/or a relative abundance of bacteria in a sample obtained from the animal, wherein the bacteria are selected from the list comprising (i) bacteria of the genus *Sphaerochaeta*, and/or (ii) bacteria of the genus *Treponema*, and/or (iii) bacteria of the genus *Anaerovorax* and/or (iv) bacteria of the genus *Mobilitalea*, and/or (v) bacteria of the phylum *Actinobacteria*, and/or (vi) bacteria of the phylum *Spirochaetes*, and/or (vii) fibre-fermenting bacteria;

b) identifying the animal as having a Body Condition Scoring (BCS) value of at least 6, wherein the fecal sample obtained from the animal comprises the abundance and/or relative abundance of bacteria that is indicative of a weight loss propensity; and c) restricting caloric intake through a calorie-restricted diet plan, wherein the calorie-restricted diet plan has a duration of from about 7 weeks to about 16 weeks, and wherein the calorie-restricted diet plan comprises dry matter in an amount from about 1% to about 1.50% relative to the animal's body mass per day during the period of caloric restriction, and wherein the calorie-restricted diet plan reduces body mass ranging from about 1.14% to about 1.25% per week.

7. The method of claim 6, wherein an abundance of bacteria of the genus *Sphaerochaeta* in the sample of less than logio 2.5 counts, and/or a relative abundance of less than 0.05%, is predictive of loss of at least 8% outset body mass after the period of caloric restriction.

8. The method of claim 6, wherein an abundance of bacteria of the genus *Mobilitalea*in the sample of less than logio 2.5 counts, and/or a relative abundance of less than 0.03%, is predictive of loss of at least 8% outset body mass after the period of caloric restriction.

9. The method of claim 6, wherein a relative abundance of bacteria of the genus *Treponema* in the sample of less than 1.7% is predictive of loss of at least 8% outset body mass after the period of caloric restriction.

10. The method of claim 6, wherein a relative abundance of bacteria of the genus *Anaerovorax* in the sample of less than 0.11% is predictive of loss of at least 8% outset body mass after the period of caloric restriction.

11. The method of claim 6, wherein an abundance of bacteria of the phylum *Actinobacteria* in the sample of less than logio 3.7 counts is predictive of loss of at least 8% outset body mass after the period of caloric restriction.

12. The method of claim 6, wherein a relative abundance of bacteria of the phylum *Spirochaetes* in the sample less than 2.3% is predictive of loss of at least 8% outset body mass after the period of caloric restriction.

13. The method of claim 6, wherein the sample is a fecal sample, blood sample or urine sample, or a sample from the gastrointestinal lumen.

14. The method of claim 13, wherein the sample from the gastrointestinal lumen is an ileal, jejunal, duodenal or colonic sample.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: 16s rDNA Forward primer

<400> SEQUENCE: 1
agagtttgat cctggctcag                                              20
```

-continued

```
<210> SEQ ID NO 2
<211> LENGTH: 25
<212> TYPE: DNA
<213> ORGANISM: Artificial Sequence
<220> FEATURE:
<223> OTHER INFORMATION: 16s rDNA Reverse primer

<400> SEQUENCE: 2
acgagtgcgt ctgctgccty ccgta                                                      25
```